(12) United States Patent
Hannen et al.

(10) Patent No.: US 12,286,609 B2
(45) Date of Patent: Apr. 29, 2025

(54) SKIN CULTURING APPARATUS AND METHOD

(71) Applicant: QUEEN MARY UNIVERSITY OF LONDON, London (GB)

(72) Inventors: Rosalind Francesca Hannen, London (GB); Jose Rafael Castrejón-Pita, London (GB)

(73) Assignee: QUEEN MARY UNIVERSITY OF LONDON, London (GB)

( * ) Notice: Subject to any disclaimer, the term of this patent is extended or adjusted under 35 U.S.C. 154(b) by 1025 days.

(21) Appl. No.: 17/285,960

(22) PCT Filed: Oct. 16, 2019

(86) PCT No.: PCT/GB2019/052952
§ 371 (c)(1),
(2) Date: Apr. 16, 2021

(87) PCT Pub. No.: WO2020/079431
PCT Pub. Date: Apr. 23, 2020

(65) Prior Publication Data
US 2021/0380912 A1 Dec. 9, 2021

(30) Foreign Application Priority Data
Oct. 17, 2018 (GB) .................................. 1816911

(51) Int. Cl.
| C12M 3/00 | (2006.01) |
| C12M 1/00 | (2006.01) |
| C12M 1/34 | (2006.01) |
| C12N 5/071 | (2010.01) |
| G01N 33/50 | (2006.01) |

(52) U.S. Cl.
CPC ............ *C12M 21/08* (2013.01); *C12M 23/48* (2013.01); *C12M 29/00* (2013.01); *C12M 29/04* (2013.01); *C12M 29/20* (2013.01); *C12M 41/14* (2013.01); *C12M 41/26* (2013.01); *C12M 41/34* (2013.01); *C12M 41/44* (2013.01); *C12N 5/0698* (2013.01); *G01N 33/5088* (2013.01); *C12N 2500/02* (2013.01)

(58) Field of Classification Search
CPC ...... C12M 21/08; C12M 23/48; C12M 29/00; C12M 29/04; C12M 29/20; C12M 41/14; C12M 41/26; C12M 41/34; C12M 41/44; C12M 25/02; C12M 23/50; C12M 41/12; C12N 5/0698; C12N 2500/02; C12N 2503/02; G01N 33/5088; G01N 33/5005; C12Q 1/68; C12Q 2600/158
See application file for complete search history.

(56) References Cited

U.S. PATENT DOCUMENTS

| 7,247,423 | B2 | 7/2007 | Scott | |
|---|---|---|---|---|
| 2002/0168768 | A1 | 11/2002 | Comer et al. | |
| 2006/0057558 | A1 | 3/2006 | Scott | |
| 2011/0111504 | A1* | 5/2011 | Knebel | C12M 29/12 435/395 |
| 2011/0159582 | A1* | 6/2011 | Israelowitz | C12M 23/48 435/293.1 |
| 2015/0132737 | A1 | 5/2015 | Descargues | |
| 2017/0269066 | A1 | 9/2017 | Osman-Ponchet | |
| 2019/0231824 | A1 | 8/2019 | Muraguchi et al. | |

FOREIGN PATENT DOCUMENTS

| CN | 105176815 | | 12/2015 |
|---|---|---|---|
| CN | 105368712 | | 3/2016 |
| CN | 105368712 A | * | 3/2016 |
| EP | 3476933 | | 5/2019 |
| JP | 2015-529817 | | 10/2015 |
| JP | 2017-184659 | | 10/2017 |
| WO | WO 2014/028734 | | 2/2014 |
| WO | WO 2014/182655 | | 11/2014 |
| WO | WO 2016/016230 | | 2/2016 |
| WO | WO 2016/039687 | | 3/2016 |
| WO | WO 2017/198988 | | 11/2017 |
| WO | WO 2018/020970 | | 2/2018 |
| WO | WO 2018/030958 | | 2/2018 |
| WO | WO 2018/130998 | | 7/2018 |

OTHER PUBLICATIONS

Episkin, "T-Skin™/ Human Full Thickness Model". archived Aug. 28, 2017 (retreived online Apr. 24, 2024 from <URL:www.episkin.com/T-Skin>), 1 page. (Year: 2017).*
Abd et al. "Skin models for the testing of transdermal drugs," Clinical Pharmacology: Advances and Applications, 2016, vol. 8, pp. 163-176.
Alepee et al. "State-of-the-Art of 3D Cultures (Organs-on-a-Chip) in Safety Testing and Pathophysiology," ALTEX, 2014, vol. 31, No. 4, pp. 441-477.
Boer et al. "Structural and biophysical characteristics of human skin in maintaining proper epidermal barrier function," Advances in Dermatology and Allergology, 2016, vol. 33, No. 1, pp. 1-5.
Borowiec et al. "Optimal Differentiation of In Vitro Keratinocytes Requires Multifactorial External Control," PLOS One, Oct. 2013, vol. 8, No. 10, article e77507, 15 pages.

(Continued)

*Primary Examiner* — Aaron J Kosar
(74) *Attorney, Agent, or Firm* — Sheridan Ross P.C.

(57) ABSTRACT

The invention provides a skin culturing apparatus configured for biphasic culturing of mammalian skin and/or a mammalian skin substitute. The apparatus comprises a first chamber that is configured to provide a gaseous environment having a relative humidity below 90% and comprising less than 5% $CO_2$, and a second chamber that is configured to provide tissue culture medium at a temperature of 33.0-37.5° C. and pH of 6.1-7.9. The invention also provides methods for culturing mammalian skin and/or skin substitutes, as well as methods for testing mammalian skin and/or mammalian skin substitutes cultured in the skin culturing apparatus.

18 Claims, 13 Drawing Sheets

(56) References Cited

OTHER PUBLICATIONS

Bouwstra et al. "Water Distribution and Natural Moisturizer Factor Content in Human Skin Equivalents Are Regulated by Environmental Relative Humidity," Journal of Investigative Dermatology, 2008, vol. 128, pp. 378-388.
Brohem et al. "Artificial skin in perspective: concepts and applications," Pigment Cell & Melanoma Research, Feb. 2011, vol. 24, No. 1, pp. 35-50.
Dezest et al. "Oxidative damage and impairment of protein quality control systems in keratinocytes exposed to a volatile organic compounds cocktail," Scientific Reports, 2017, vol. 7, article 10707, 14 pages.
Duracher et al. "In vitro and in vivo dermal absorption assessment of acetyl aspartic acid: a compartmental study," International Journal of Cosmetic Science, 2015, vol. 37, Supplement 1, pp. 34-40.
Eedy "Dermatology: a specialty in crisis," Clinical Medicine, 2015, vol. 15, No. 6, pp. 509-510.
Fentem et al. "ECVAM's Activities in Validating Alternative Tests for Skin Corrosion and Irritation," Alternatives to Laboratory Animals, 2002, vol. 30, Supplement 2, pp. 61-67.
Geiser et al. "Evaluating Adverse Effects of Inhaled Nanoparticles by Realistic In Vitro Technology," Nanomaterials, 2017, vol. 7, No. 2, Article 49, 15 pages.
Hollestein et al. "An Insight into the Global Burden of Skin Diseases," Journal of Investigative Dermatology, 2014, vol. 134, pp. 1499-1501.
Huh et al. "Reconstituting Organ-Level Lung Functions on a Chip," Science, Jun. 2010, vol. 328, pp. 1662-1668.
Jungersted et al. "Lipids and skin barrier function—a clinical perspective," Contact Dermatitis, 2008, vol. 58, pp. 255-262.
Katayama et al. "Gene expression analysis of skin grafts and cultured keratinocytes using synthetic RNA normalization reveals insights into differentiation and growth control," BMC Genomics, 2015, vol. 16, Article 476, 14 pages.
Kubo et al. "The stratum corneum comprises three layers with distinct metal-ion barrier properties," Scientific Reports, 2013, vol. 3, Article 1731, 11 pages.
Mathes et al. "The use of skin models in drug development," Advanced Drug Delivery Reviews, 2014, vol. 69-70, pp. 81-102.
Parenteau et al. "The organotypic culture of human skin keratinocytes and fibroblasts to achieve form and function," Cytotechnology, 1992, vol. 9, pp. 163-171.
Ponec et al. "Lipid and ultrastructural characterization of reconstructed skin models," International Journal of Pharmaceutics, 2000, vol. 203, pp. 211-225.
Prunieras et al. "Methods for Cultivation of Keratinocytes with an Air-Liquid Interface," The Journal of Investigative Dermatology, 1983, vol. 81, No. 1 Supplement, pp. 28s-33s.
Schafer-Korting et al. "Reconstructed Human Epidermis for Skin Absorption Testing: Results of the German Prevalidation Study," Alternatives to Laboratory Animals, 2006, vol. 34, pp. 283-294.
Sriram et al. "Full-thickness human skin-on-chip with enhanced epidermal morphogenesis and barrier function," Materials Today, May 2018, vol. 21, No. 4, pp. 326-340.
Takei et al. "Low environmental humidity induces synthesis and release of cortisol in an epidermal organotypic culture system," Experimental Dermatology, 2013, vol. 22, pp. 662-664.
Wever et al. "Human Skin Models for Research Applications in Pharmacology and Toxicology: Introducing NativeSkin®, the "Missing Link" bridging Cell Culture and/or Reconstructed Skin Models and Human Clinical Testing," Applied In Vitro Toxicology, 2015, vol. 1, No. 1, pp. 26-32.
Wufuer et al. "Skin-on-a-chip model simulating inflammation, edema and drug-based treatment," Scientific Reports, 2016, vol. 6, Article 37471, 12 pages.

* cited by examiner

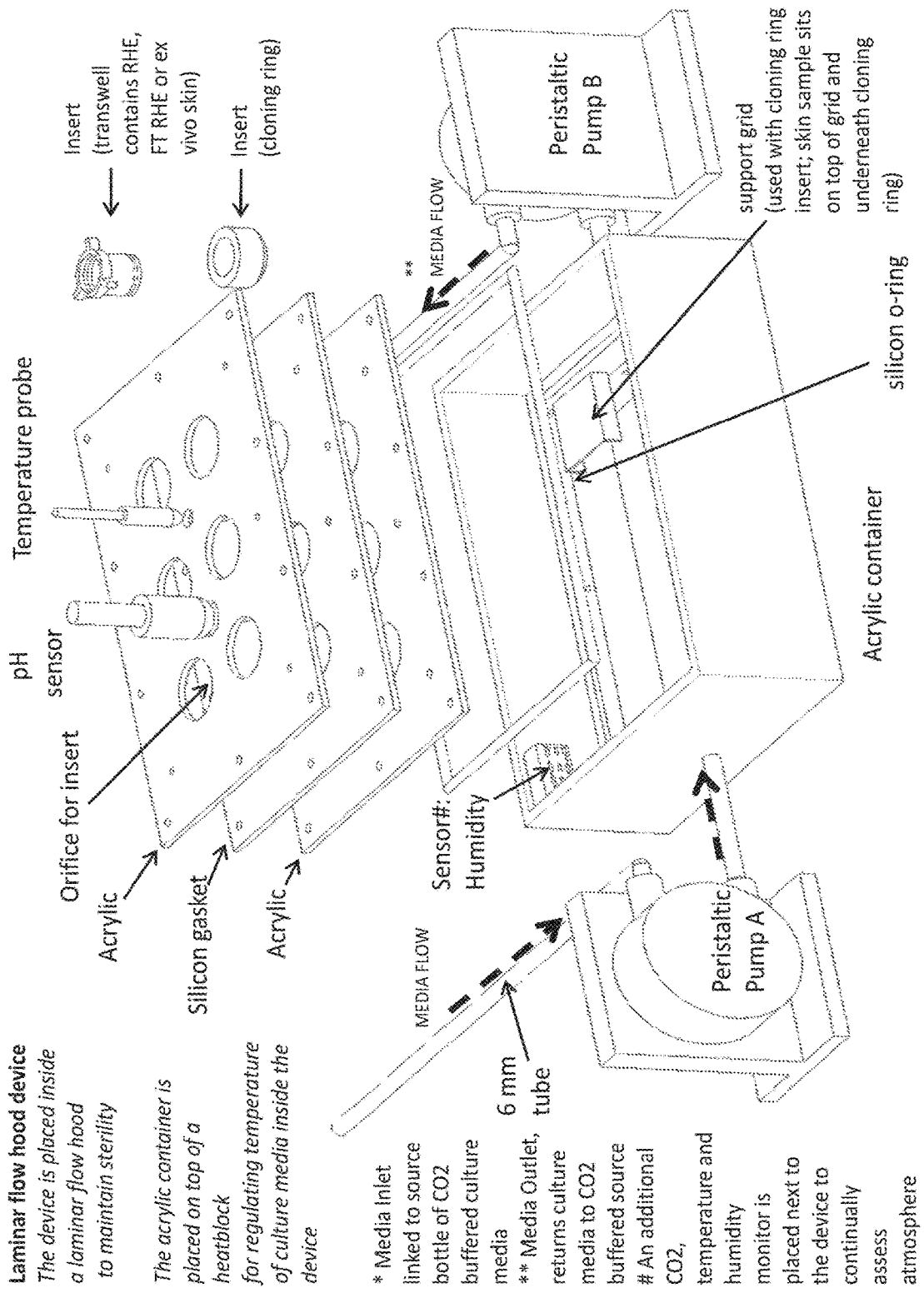

SKIN CULTURING APPARATUS AND METHOD

CROSS REFERENCE TO RELATED APPLICATIONS

This application is a national stage application under 35 U.S.C. 371 and claims the benefit of PCT Application No. PCT/GB2019/052952 having an international filing date of 16 Oct. 2019, which designated the United States, which PCT application claimed the benefit of Great Britain Patent Application No. 1816911.0, filed 17 Oct. 2018, the disclosures of which are hereby incorporated by reference in their entireties.

FIELD OF THE INVENTION

The present invention relates to a skin culturing apparatus configured for biphasic culturing of ex vivo mammalian skin and/or a mammalian skin substitute. It also relates to methods for culturing ex vivo mammalian skin and/or skin substitutes. The invention further relates to methods for testing the effect of a compound or composition on ex vivo mammalian skin and/or a mammalian skin substitute; assessing the barrier function of ex vivo mammalian skin and/or a mammalian skin substitute; assessing immune function and/or inflammation of ex vivo mammalian skin and/or a mammalian skin substitute; and assessing genomic, transcriptomic, metabolomic, lipidomic and/or proteomic response in ex vivo mammalian skin and/or a mammalian skin substitute. The invention also relates to methods for assessing dermal absorption of ex vivo mammalian skin and/or a mammalian skin substitute; methods for assessing skin sensitization and/or skin irritation; and methods for testing the effect of a gas, aerosol or pollutant.

BACKGROUND OF THE INVENTION

Globally, skin diseases form the fourth leading cause of all non-fatal disease burden and in the UK 54% of the population suffers from a skin disease. The desire for improved skin models has been driven by the cosmetics industry and by the clinic for transplantation of in vitro-grown tissue substitutes.

Through regulatory pressures on animal testing, the cosmetic industry has predominantly driven developments of human 3D-skin equivalents also known as recombinant human epidermis (RHE), which range from using just keratinocytes to full thickness RHE (FT RHE) that includes a dermal matrix typically made of collagen and dermal fibroblasts and keratinocytes forming an epidermal layer on top. Unfortunately, RHE is a poor mimic of in vivo skin. FT RHE also fails to accurately mimic many features of in vivo human skin. Limitations of FT RHE models include (1) hyperproliferation—including the expression of cytokeratin 16 (K16), a hyperproliferation marker not expressed in healthy skin except palmar-plantar skin; (2) incomplete barrier formation due to lipid abnormalities, which causes (3) reduced barrier properties that inaccurately estimate pharmacological penetration; (4) absence of skin appendages; (5) absence/limited immune cell incorporation (although there are now a number of models attempting to address immune cell incorporation); (6) reduced expression of xenobiotic metabolic enzymes, e.g. P450 enzymes, indicating impairment of normal skin function. Currently, the Scientific Committee on Consumer Safety (SCCS) guidelines consider all in vitro reconstructed human skin models as inadequate for assessing dermal absorption of cosmetic ingredients.

As a result, ex vivo human skin is still considered to be the gold standard for skin testing, although it is subject to limited accessibility and inter-patient variability. However, ex vivo human skin rapidly degrades in culture such that OECD guidelines (OECD 428) stipulate ex vivo skin should not exceed 24 h for skin irritant testing. Intact whole skin rapidly loses barrier function (within 24-72 hours), cell proliferation (48-72 hours) and resident immune cells rapidly leach from the tissue (2-4 days). Consequently, extracted whole skin loses integrity from 24 h, affecting its ability to be used for screening and drug testing (OECD 428). A commercialised culture media and matrix developed by Genoskin for supporting ex vivo skin culture (Native-Skin®) can retain some resident immune cells, although quantification is lacking, and it is reported to have improved barrier function compared to FT RHE models. However, this system has yet to be approved by the OECD due to inter-patient variability. Both healthy FT RHE and ex vivo skin also exhibit features of partial wounding profiles, indicated by their transcription profiles and activation of K16 expression. Thus, current methods represent a semi-wounded rather than healthy state. Accordingly, there is a great need to improve human testing platforms. Reports suggest 9 out of 10 candidate medicines pass safety and efficacy animal studies only to fail when administered to humans.

Prior art ex vivo and RHE (including FT RHE) skin culture methods typically rely on standard tissue culture incubators in which the ex vivo mammalian skin and/or skin substitute is maintained at 37° C., 5-10% $CO_2$ and 90-100% relative humidity. Some publications refer to the culture of ex vivo skin or FT RHE at an "air-liquid" interface, in which the liquid is tissue culture medium and "air" is the internal atmosphere of the tissue culture incubator, having a temperature of 37° C. and a relative humidity of 90-100% and comprising 5-10% $CO_2$. The presence of 5-10% $CO_2$ in the gaseous phase of such incubators enables the pH of the tissue culture medium to be maintained at an appropriate level for the culture of ex vivo mammalian skin and/or a mammalian skin substitute. In some reports, the use of tissue culture incubators is not described because the method is an assumed standard. Indeed, if a tissue culture incubator were not used, further description in the report would be required to describe how pH regulation of the culture media is achieved.

A skin culture method and apparatus that circumvents many of these limitations of standard skin culture practice for both ex vivo skin and skin substitutes, such as RHE and FT RHE, is required to advance skin culture models for all dermatology applications within pharmaceutical, cosmetic and academic settings.

SUMMARY OF THE INVENTION

The present invention provides, in a first aspect, a skin culturing apparatus configured for biphasic culturing of ex vivo mammalian skin or a mammalian skin substitute comprising a first chamber, a second chamber, a barrier, and a skin sample holder, wherein: the first chamber is configured to provide a gaseous environment having a relative humidity below 90% and comprising less than 5% $CO_2$; the second chamber is configured to provide tissue culture medium at a temperature of 33.0-37.5° C. and pH of 6.1-7.9; the skin sample holder is configured to house ex vivo mammalian skin and/or a mammalian skin substitute; and the barrier separates the first and second chambers, and is configured to receive the skin sample holder; wherein in use: (i) the first chamber comprises a gaseous environment having a relative humidity below 90% and comprising less than 5% $CO_2$; (ii) the second chamber comprises a tissue culture medium at a temperature of 33.0-37.5° C. and pH of 6.1-7.9; (iii) the skin sample holder houses ex vivo mammalian skin and/or a mammalian skin substitute; (iv) a first surface of the ex vivo mammalian skin or skin substitute is exposed to the gaseous environment, but not to the tissue culture medium; and (v) a second surface of the ex vivo mammalian skin or skin substitute is exposed to the tissue culture medium, but not to the gaseous environment.

The present invention provides, in a second aspect, a method of culturing ex vivo mammalian skin and/or a mammalian skin substitute, the method comprising providing ex vivo mammalian skin and/or a mammalian skin substitute and culturing the ex vivo mammalian skin and/or skin substitute using the apparatus of the invention. The invention also provides ex vivo mammalian skin and/or a mammalian skin substitute which has been cultured according to said method.

The present invention provides, in a third aspect, a method of culturing ex vivo mammalian skin and/or a mammalian skin substitute, said method comprising maintaining a first surface of the ex vivo mammalian skin or skin substitute in a gaseous environment comprising less than 5% $CO_2$, at a temperature below 37° C. and a relative humidity below 90%; and maintaining a second surface of the ex vivo mammalian skin or skin substitute in a tissue culture medium at a temperature of 33.0-37.5° C. and pH of 6.1-7.9; wherein the first surface is not exposed to the tissue culture medium; and the second surface is not exposed to the gaseous environment. The invention also provides ex vivo mammalian skin and/or a mammalian skin substitute which has been cultured according to said method.

The present invention provides, in a fourth aspect, a method for testing the effect of a compound or composition on ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method of the invention; (c) contacting said ex vivo mammalian skin and/or skin substitute with the compound or composition; and (d) determining the effect of the compound or composition on the ex vivo mammalian skin and/or skin substitute.

The present invention provides, in a fifth aspect, a method for assessing the barrier function of ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method of the invention; (c) contacting said ex vivo mammalian skin and/or skin substitute with the compound or composition; and (d) determining to what extent the compound or composition can pass through the ex vivo mammalian skin and/or skin substitute.

The present invention provides, in a sixth aspect, a method for assessing immune function and/or inflammation in ex vivo mammalian skin and/or a mammalian skin substitute, comprising: (a) providing ex vivo mammalian skin and/or a mammalian skin substitute; (b) culturing the ex vivo mammalian skin and/or skin substitute using a method of the invention; (c) contacting said ex vivo mammalian skin and/or skin substitute with an allergen or immunogen; and (d) determining whether an immune response or inflammation of the ex vivo mammalian skin and/or skin substitute occurs.

The present invention provides, in a seventh aspect, a method for assessing the genomic, transcriptomic, metabolomic, lipidomic and/or proteomic response of ex vivo mammalian skin and/or a mammalian skin substitute to a stimulus, comprising: (a) providing ex vivo mammalian skin and/or a mammalian skin substitute; (b) culturing the ex vivo mammalian skin and/or skin substitute using a method of the invention; (c) exposing said ex vivo mammalian skin and/or skin substitute to a stimulus; and (d) determining the genomic, transcriptomic, metabolomic, lipidomic and/or proteomic response of the ex vivo mammalian skin and/or skin substitute to said stimulus.

The present invention provides, in an eighth aspect, a method for conducting genomic, transcriptomic, metabolomic, lipidomic and/or proteomic analysis of ex vivo mammalian skin and/or a mammalian skin substitute, comprising: (a) providing ex vivo mammalian skin and/or a mammalian skin substitute; (b) culturing the ex vivo mammalian skin and/or skin substitute using a method according to the invention; (c) conducting genomic, transcriptomic, metabolomic, lipidomic and/or proteomic assays on the ex vivo mammalian skin and/or skin substitute.

The present invention provides, in an ninth aspect, a skin culturing apparatus configured for biphasic culturing of ex vivo mammalian skin or a mammalian skin substitute comprising a first chamber, a second chamber, a barrier, and a skin sample holder, wherein: the first chamber is configured to provide a gaseous environment having a relative humidity below 90% and comprising less than 5% $CO_2$; the second chamber is configured to provide tissue culture medium at a temperature of 33.0-37.5° C. and pH of 6.1-7.9; the skin sample holder is configured to house ex vivo mammalian skin and/or a mammalian skin substitute; and the barrier separates the first and second chambers, and is configured to receive the skin sample holder; wherein in use: (i) the first chamber comprises a gaseous environment having a relative humidity below 90% and comprising less than 5% $CO_2$; (ii) the second chamber comprises a tissue culture medium at a temperature of 33.0-37.5° C. and pH of 6.1-7.9; (iii) the skin sample holder houses ex vivo mammalian skin and/or a mammalian skin substitute; (iv) a first surface of the ex vivo mammalian skin or skin substitute is exposed to the gaseous environment, but not to the tissue culture medium; and (v) a second surface of the ex vivo mammalian skin and/or skin substitute, which opposes said first surface, is exposed to the tissue culture medium, but not to the gaseous environment, wherein the apparatus comprises: (a) a housing that encloses the first and second chambers; (b) an inflow pipe which is configured to deliver compressed air or medical air into the first chamber; (c) a filter outlet which is configured to enable the release of gases; (d) one or more pumps which pump tissue culture medium into and/or out of the second chamber, e.g. at a flow rate of between 1 and 45 ml/min; (e) one or more $CO_2$ sensor(s), temperature probe(s) and/or humidity sensor(s) in the first chamber; (f) one or more temperature probe(s) in the second chamber; (g) means for maintaining the tissue culture medium at a controlled depth within the second chamber; and/or (h) means for providing feedback control of humidity, temperature and/or tissue culture medium pH.

The present invention provides, in an tenth aspect, a method for assessing dermal absorption of ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention; (c) contacting said ex vivo mammalian skin and/or skin substitute with a compound or composition; and (d) determining to what extent the compound or composition is absorbed by the ex vivo mammalian skin and/or skin substitute.

The present invention provides, in a eleventh aspect, a method for assessing skin sensitization and/or skin irritation in an ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention; (c) contacting said ex vivo mammalian skin and/or skin substitute with a compound or composition or exposing said ex vivo mammalian skin and/or skin substitute to irradiation; and (d) determining whether skin sensitization and/or skin irritation occurs in the ex vivo mammalian skin and/or skin substitute.

The present invention provides, in a twelfth aspect, a method for testing the effect of a gas, aerosol or pollutant on ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention; (c) contacting said ex vivo mammalian skin and/or skin substitute with said gas, aerosol or pollutant; and (d) determining the effect of said gas, aerosol or pollutant on the ex vivo mammalian skin and/or skin substitute.

The present invention provides, in a thirteenth aspect, ex vivo mammalian skin and/or a mammalian skin substitute which has been cultured according to methods of the invention.

The present invention provides, in a fourteenth aspect, a method for testing the effect of air pollution and/or radiation on ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention; (c) delivering an environmental/atmospheric source of pollution to the ex vivo mammalian skin and/or skin substitute and/or exposing the mammalian skin and/or mammalian skin substitute to radiation; and (d) analyzing the effect of step (c) on skin immune, inflammatory, toxicology, viability, metabolism, barrier function, genetic, epigenetic, proteomic or lipidomic responses, wherein optionally said radiation is electromagnetic and/or ionizing radiation.

The present invention provides, in a fifteenth aspect, a method for assessing the effect of low oxygen levels on ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention, wherein the oxygen levels is the gaseous environment and/or tissue culture medium are maintained at less than 21%, optionally at less than 20%, 19%, 18%, 17%, 16%, 15%, 14%, 13%, 12%, 11%, 10%, 9%, 8%, 7%, 6%, 5%, 4%, 3%, 2% or 1%; (d) analyzing the effect of said low oxygen levels on skin immune, inflammatory, toxicology, viability, metabolism, barrier function, genetic, epigenetic, proteomic or lipidomic responses.

The present invention provides, in a sixteenth aspect, a method for assessing the effect of a medical aesthetic device and/or wearable medical device on ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention; wherein a medical aesthetic device and/or wearable medical device is used on said ex vivo mammalian skin and/or skin substitute; (e) analyzing the effect of said medical aesthetic device or wearable medical device on skin immune, inflammatory, toxicology, viability, metabolism, barrier function, genetic, epigenetic, proteomic or lipidomic responses.

The present invention provides, in a seventeenth aspect, a method for assessing the efficacy and/or safety of skin implants, the method comprising: (a) providing ex vivo mammalian skin and/or a mammalian skin substitute; (b) culturing the ex vivo mammalian skin and/or skin substitute using a method according to the invention; (c) delivering said skin implant to mammalian skin and/or a mammalian skin substitute; (d) analyzing the effect of said skin implant on skin immune, inflammatory, toxicology, viability, metabolism, barrier function, genetic, epigenetic, proteomic or lipidomic responses, wherein optionally said implant is a microchip, e.g. an NFC and RFID chips, a chemical or tattoo sensor, a topical and/or an injectable sensor.

The present invention provides, in a eighteenth aspect, a method for repeat dose testing of a chemical, compound or aerosol, the method comprising: (a) providing ex vivo mammalian skin and/or a mammalian skin substitute; (b) culturing the ex vivo mammalian skin and/or skin substitute using a method according to the invention; (c) dosing of a chemical, compound or aerosol, which is repeated more than once and/or over a period longer than 24 h, to the ex vivo mammalian skin and/or a mammalian skin substitute; and (d) analyzing the skin immune, inflammatory, toxicology, viability, metabolism, barrier function, genetic, epigenetic, proteomic and lipidomic responses before, during and/or after the skin exposure to repeat dosing of a chemical, compound or aerosol.

The present invention provides, in a nineteenth aspect, a method for assessing responses to disruption of ex vivo mammalian skin and/or skin substitute, such as wound healing, wherein the method comprises: (a) providing ex vivo mammalian skin and/or a mammalian skin substitute; (b) culturing the ex vivo mammalian skin and/or skin substitute using a method according to the invention; (c) disrupting the epidermis and/or dermis of the ex vivo mammalian skin and/or skin substitute, for example by punch biopsy, cutting or abrasion; and (d) analyzing the skin immune, inflammatory, toxicology, viability, metabolism, barrier function, genetic, epigenetic, proteomic and lipidomic responses before, during and/or after the skin wound healing response.

The present invention provides, in a twentieth aspect, a method for assessing the skin microbiome and/or effects of bacterial, fungal, viral exposure to skin, the method comprising: (a) providing ex vivo mammalian skin and/or a mammalian skin substitute; (b) culturing the ex vivo mammalian skin and/or skin substitute using a method according to the invention; (c) assessing skin microbiome levels in said ex vivo mammalian skin and/or skin substitute; (d) introducing bacteria, fungi and/or viruses to the apparatus; (e) analyzing the effect of said bacteria, fungi and/or viruses on skin immune, inflammatory, toxicology, viability, metabolism, barrier function, genetic, epigenetic, proteomic or lipidomic responses.

The present invention provides, in a twenty-first aspect, a method for assessing skin permeation, corrosion, pigmentation and/or photosensitivity of ex vivo mammalian skin and/or a mammalian skin substitute, the method comprising: (a) providing ex vivo mammalian skin and/or a mammalian skin substitute; (b) culturing the ex vivo mammalian skin and/or skin substitute using a method according to the invention; (c) exposing the ex vivo mammalian skin and/or skin substitute to a chemical, a compound and/or a form of assault or irradiation; and (d) assessing skin permeation, corrosion, pigmentation and/or photosensitivity of the ex vivo mammalian skin and/or a mammalian skin substitute.

The present invention provides, in a twenty-second aspect, a method for developing computational analysis of skin function and metabolism, the method comprising: (a) providing ex vivo mammalian skin and/or a mammalian skin substitute; (b) culturing the ex vivo mammalian skin and/or skin substitute using a method according to the invention; (c) assessing skin function and metabolism; and (d) conducting computational analysis of data outputs for interpreting and predicting skin function and metabolism.

Embodiments of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first or twenty-second aspects include the following features:
- (i) (a) the first chamber comprises a gaseous environment having a relative humidity below 90% and comprising less than 5% $CO_2$, wherein optionally said gaseous environment is provided by an inflow of compressed air or medical air into the first chamber; and/or (b) the second chamber comprises tissue culture medium at a temperature of 33.0-37.5° C., preferably at about 37° C., and a pH of 6.1-7.9; and/or (c) the skin sample holder houses ex vivo mammalian skin and/or a mammalian skin substitute;
- (ii) said the epidermis of ex vivo mammalian skin or epidermis-equivalent of a mammalian skin substitute provides the first surface; and/or the dermis of ex vivo mammalian skin or dermis-equivalent of a mammalian skin substitute provides the second surface;
- (iii) the apparatus comprises ex vivo mammalian skin or a mammalian skin substitute, optionally wherein the skin substitute is recombinant human epidermis (RHE) or full thickness RHE (FT RHE);
- (iv) the ex vivo mammalian skin and/or skin substitute comprises stratum corneum, stratum granulosum, stratum spinosum and/or a stratum basale layers;
- (v) in use: the stratum corneum layer is exposed to the gaseous environment, but not to the tissue culture medium; and/or the stratum basale layer and/or the dermis or dermal equivalent is exposed to the tissue culture medium, but not to the gaseous environment;
- (vi) the ex vivo mammalian skin and/or skin substitute is one of a plurality of ex vivo mammalian skin and/or skin substitute samples, wherein the plurality of samples are arranged in separate skin sample holders in an array format;
- (vii) the apparatus comprises one or more pumps, which pump tissue culture medium into and/or out of the second chamber, wherein optionally the flow rate is between 1 and 45 ml/min;
- (viii) the apparatus comprises one or more pH probe(s), temperature probe(s), $CO_2$ sensor(s), and/or humidity sensor(s);
- (ix) in use the tissue culture medium is maintained at a controlled depth within the second chamber;
- (x) the barrier comprises a gasket, e.g. a silicon gasket, or an o-ring;
- (xi) the second chamber comprises tissue culture medium and said tissue culture medium is maintained at a temperature of 33.0-37.5° C. by the action of a heater;
- (xii) said apparatus provides monitoring and feedback control of culture media pH, humidity and/or temperature;
- (xiii) the apparatus comprises a housing that encloses the first and second chambers;
- (xiv) the apparatus comprises an inflow pipe which is configured to deliver gases into the first chamber, wherein optionally said gases comprise compressed air or medical air; and/or the housing additionally comprises a filter outlet, which is configured to enable the release of gases.
- (xv) (a) immune cells are retained in the ex vivo mammalian skin and/or skin substitute following at least five days in culture; and/or (b) epidermal cells of the ex vivo mammalian skin and/or skin substitute retain a normal lipid profile following at least three days in culture; and/or (c) cells of the ex vivo mammalian skin and/or skin substitute express keratinocyte differentiation markers at normal detectible levels following at least five days in culture; and/or (d) cells of the ex vivo mammalian skin and/or skin substitute do not have elevated K16 expression following at least five days in culture relative to baseline levels;
- (xvi) the skin substitute is FT RHE or RHE;
- (xvii) the gaseous environment: (a) comprises 0.02-0.05% $CO_2$; and/or (b) has a relative humidity of 40-50% RH; and/or (c) is at a temperature of 18-25° C.; and/or (d) is sterile.
- (xviii) the tissue culture medium: (a) flows under the dermis of the ex vivo skin or dermal equivalent of the FT-RHE at a flow rate ranging from 1 ml/min to 45 ml/min; and/or (b) is at a temperature of 37° C.;
- (xix) (a) immune cells are retained in the ex vivo mammalian skin and/or skin substitute following at least five days in culture; (b) epidermal cells of the ex vivo mammalian skin and/or skin substitute retain a normal lipid profile following at least three days in culture; (c) cells of the ex vivo mammalian skin and/or skin substitute express keratinocyte differentiation markers at normal detectible levels following at least five days in culture; and/or (d) cells of the ex vivo mammalian skin and/or skin substitute do not have elevated K16 expression following at least five days in culture relative to baseline levels;
- (xx) said method comprises monitoring and feedback control of the pH, humidity, temperature, and/or flow rate of tissue culture medium;
- (xxi) the compound or composition is: (i) a therapeutic compound or composition, e.g. an anti-cancer compound or composition; (ii) a pharmaceutical compound or composition, which optionally comprises a pharmaceutically acceptable carrier; (iii) a cosmetic compound or composition; (iv) a chemical substance; and/or (v) a pesticide.
- (xxii) said effect is the promotion or inhibition of hair growth; said effect comprises the treatment or prevention of a skin-related condition or disease, e.g. dermatitis or melanoma; said effect is an adverse skin reaction, e.g. wherein said method is a method for testing the toxicity of a compound or composition (e.g. a cosmetic compound or composition) for said adverse skin reaction; and/or said effect is skin sensitization, and/or skin irritation;

(xxiii) step (d) comprises measuring gene expression levels;
(xxiv) the ex vivo mammalian skin and/or skin substitute comprises a model of a disease condition;
(xxv) said skin substitute comprises immune cells, wherein optionally said skin substitute is RHE or FT RHE;
(xxvi) said apparatus comprises microfluidics and/or means for facilitating fluidic movement of the tissue culture medium that is not regulated by a pump;
(xxvii) in use, the hypodermis or adipose tissue is exposed to the tissue culture medium, but not to the gaseous environment;
(xxviii) the barrier comprises a plastic and/or silicon gasket;
(xxix) the cells retain metabolic activity/viability for at least 5 days without the need of a culture media that is metabolically active (e.g. culture media that reacts with MTT to create formazan salt that is purple in colour);
(xxx) epidermal skin surface properties of pH and moisture are maintained for 7 days;
(xxxi) the gaseous environment comprises 0.02-0.09% $CO_2$;
(xxxii) the method comprises analyzing the effect of the compound or composition on skin immune, inflammatory, toxicology, viability, metabolism, barrier function, genetic, epigenetic, proteomic or lipidomic responses;
(xxxiii) the composition comprises an injectable composition, e.g. a vaccine composition, a dermal filler, PRP (platelet rich protein), botox, etc.;
(xxxiv) the barrier comprises a plastic gasket;
(xxxv) the skin sample holder comprises a mesh and optionally the ex vivo skin or skin substitute is locatable on said mesh;
(xxxvi) the skin sample holder is a transwell insert;
(xxxvii) the skin sample or skin equivalent is: embedded in or surrounded by a gel; supported by a gel; or is inside a transwell;
(xxxviii) cells retain metabolic activity/viability for at least 5 days;
(xxxix) epidermal skin surface properties of pH and moisture are maintained for 7 days;
(xl) the tissue culture medium flows through the second chamber at a flow rate ranging from 0.01 ml/min to 45 ml/min, e.g. 0.01-10 ml/min, 0.02-10 ml/min, 0.03-10 ml/min, 0.05-10 ml/min, 0.06-10 ml/min, 0.1-10 ml/min, 0.5-10 ml/min, 0.5-1 ml/min;
(xli) the tissue culture medium is at a temperature of 33-37° C.;
(xlii) the tissue culture medium is maintained at pH 6.1-7.9; and/or
(xliii) the tissue culture medium is maintained at an oxygen saturation level of 0.2-15% $O_2$, e.g. by using monitoring and/or feedback control;
(xliv) said method comprises monitoring and/or feedback control of $CO_2$, humidity, temperature and/or flow rate within the gaseous environment; and/or
(xlv) the first surface is an epidermal cornified layer and/or the second surface is the dermis and/or hypodermis;
(xlvi) said ex vivo mammalian skin and/or skin substitute comprises one or more sensors to assess skin function and biological outputs, wherein optionally said biological output comprises impedance for skin barrier and/or tissue viability, transepidermal water loss, skin surface pH, intra- and intercellular pH, cytokines, gases (tissue oxygen, nitric oxide), glucose, small molecules, and/or peptide/protein sensors;
(xlvii) said housing is configured to allow or block the passage of all or some wavelengths of electromagnetic and/or ionising radiation, including UV radiation;
(xlviii) the gaseous environment has a relative humidity below 80%, e.g. below 75%, 70%, 65%, 60%, 55%, 50%, 45%, etc.;
(xlix) the gaseous environment comprises 0.03-0.09% $CO_2$;
(l) the gaseous environment has a temperature below 29° C.;
(li) the gaseous environment comprises medical air, atmospheric air, environmental air, polluted air, an aerosol, etc.;
(lii) the first chamber comprises desiccant(s) to aid the regulation of humidity;
(liii) flow of gases into the first chamber is regulated by an on/off valve (e.g. for pressurized gas) or a pump, fan, and/or vacuum (e.g. for non-pressurized gas), e.g. to aid gas exchange;
(liii) the apparatus comprises a heater, which may be a hotplate, heating element, heatblock and/or a water bath;
(liii) the ex vivo mammalian skin or skin substitute may be healthy or diseased skin;
(liv) the ex vivo mammalian skin and/or skin substitute comprises a model of a disease condition or change to healthy skin physiology, e.g. dandruff formation;
(lv) the epidermal cornified layer thickness of said ex vivo mammalian skin and/or skin substitute remains constant or substantially constant (e.g. within 1, 2, 3, 4, 5%, 7%, 10%, 15%, 20% or 25%), relative to said thickness at day 0, during at least 1, 2, 3, 4, 5, 6, or 7 days of culture in said apparatus; and
(n) the epidermal cornified layer thickness of said ex vivo mammalian skin and/or skin substitute remains constant, relative to said thickness at day 0, during at least 7 days of culture in said apparatus.

For the avoidance of doubt, the embodiments described herein can be combined unless context clearly dictates otherwise. Furthermore, the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first or twenty-second aspects, and the embodiments thereof can be combined with other optional features of the present invention as disclosed elsewhere herein unless context clearly dictates otherwise.

Fluidic culture media flow—ranging from 3.3 ml/min to 41.67 ml/min, closed loop system. The liquid level within the device is kept constant at the height of the liquid output by pumping out the media at a higher flow rate than the input flow. Culture media temperature is regulated at 37° C. (33-37° C.) on a hotplate. In the atmospheric air compartment, a HEPA filter allows for pressure release to prevent the buildup of gases, whilst maintaining sterility. In addition, a $CO_2$ sensor is included in the air phase, as well as a humidity sensor and temperature probe, to check $CO_2$ levels remained within healthy atmospheric internal room environment levels (below 500 ppm).

Figure 1A:
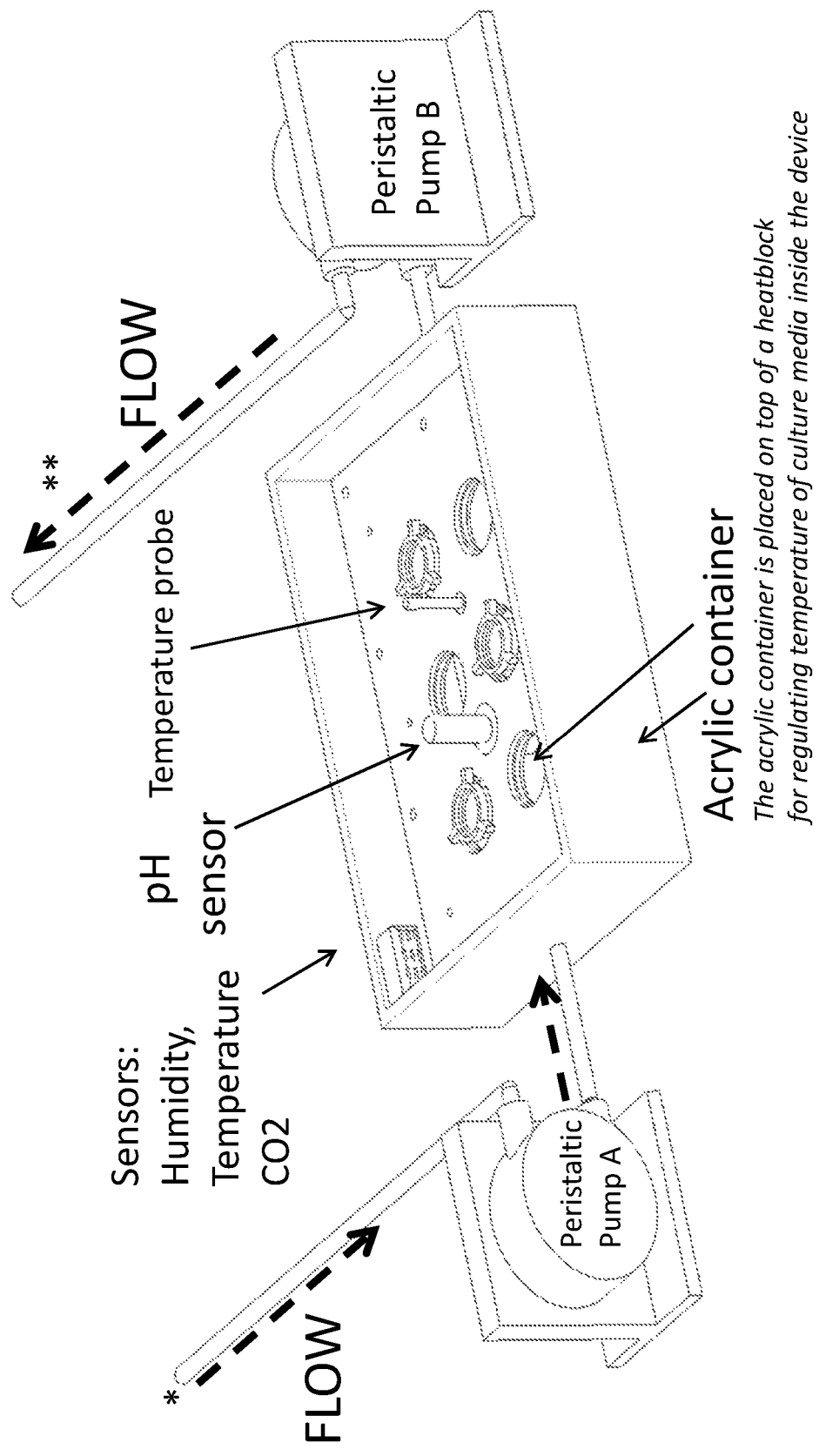
FIGS. 1A & B. 1A. Detailed schematic of the plastic ware and attachments of the laminar flow hood fluidic skin culture device; 1B Component parts of laminar flow hood fluidic skin culture device.
Figure 1C:
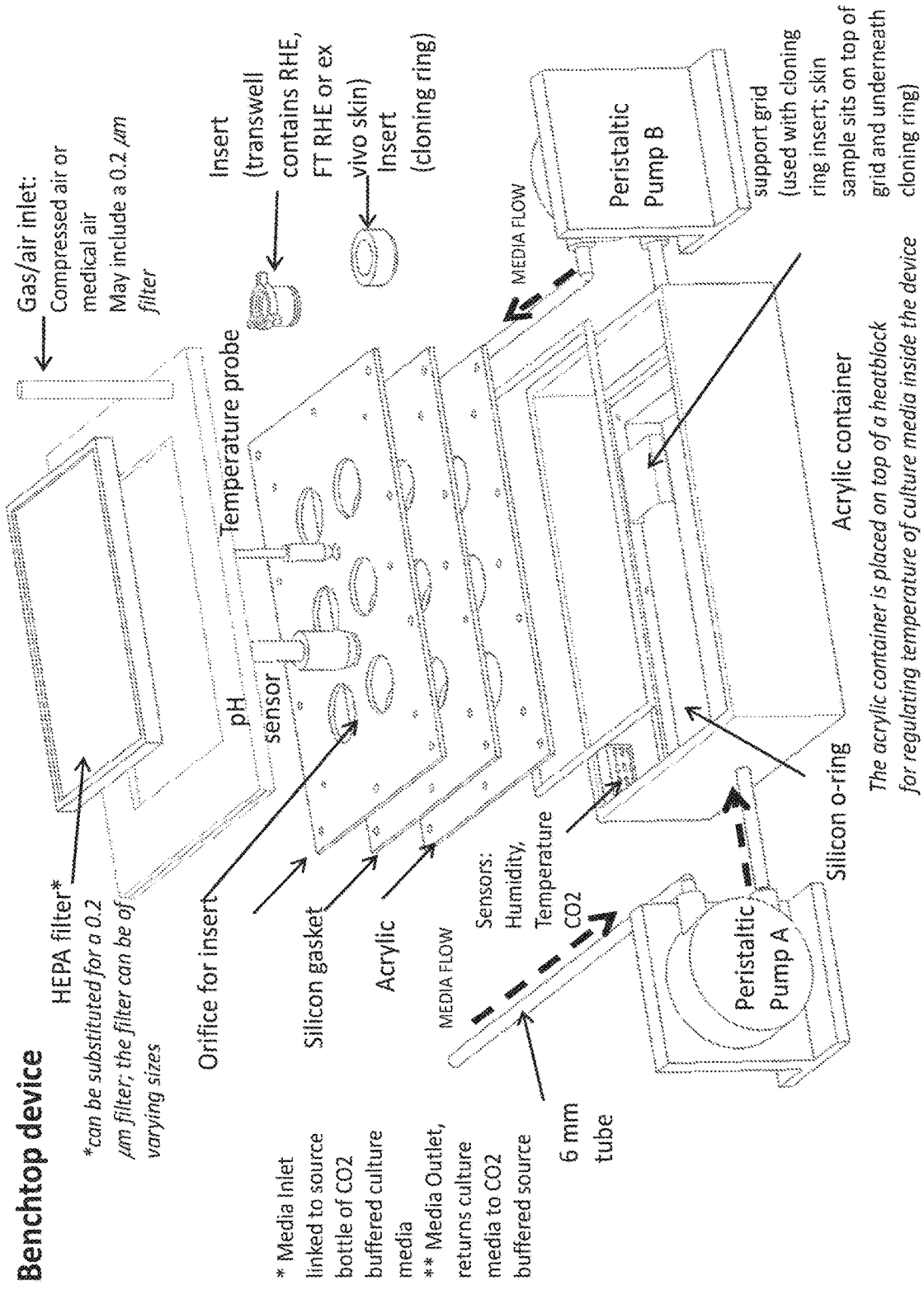
FIGS. 1C & 1E. An autoregulated benchtop device for ex vivo and FT-RHE skin culture with continuous monitoring and feedback control of 1. culture media pH, regulated between pH 7.2 and 7.4; 2. atmospheric air control linked to humidity monitors to maintain humidity between 40-45% RH. The pH is regulated by linking a pH probe that continuously monitors culture media pH to a $CO_2$ valve that opens to release $CO_2$ gas into the culture media when the pH is too basic. There is a short burst of gas release, followed by a time delay to allow for the media/$CO_2$/pH to equilibrate to determine the new pH after $CO_2$ release. The system then determines whether the valve needs to open again. If the media pH has been sufficiently buffered, the $CO_2$ valve will remain closed.
Figure 1D:
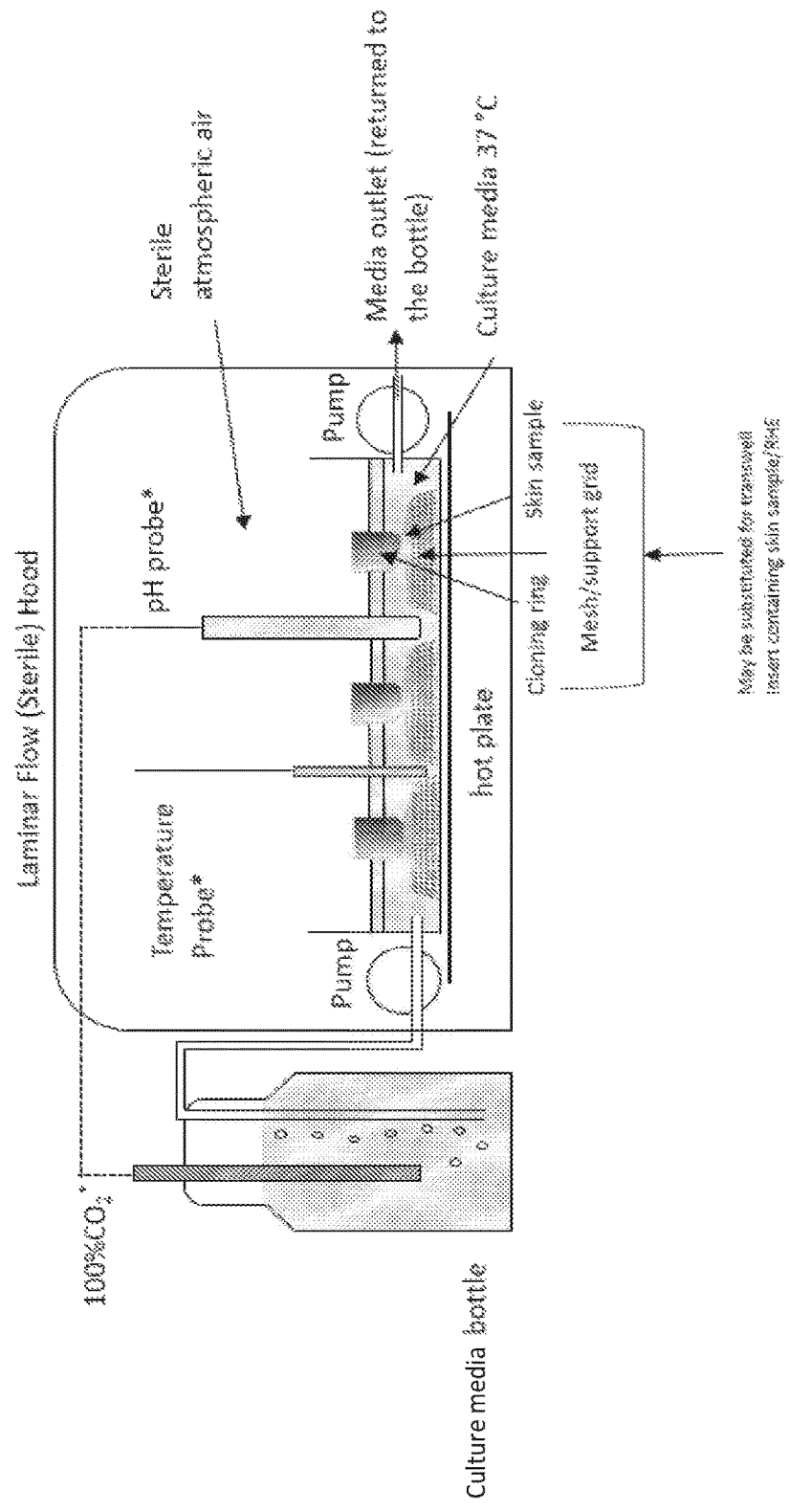
FIGS. 1B & 1D. Schematic of a device for ex vivo and FT-RHE skin culture with continuous monitoring and feedback control of culture media pH, regulated between pH 7.2 and 7.4 by a valve that opens to allow the inflow of $CO_2$ if the pH increases too much. Fluidic culture media flow—ranging from 3.3 ml/min to 41.67 ml/min in a closed loop system. Culture media temperature is regulated at 37° C. (33-37° C.) on a hotplate. A silicon gasket and/or an o-ring and plastic holders separate the fluidic tissue culture media phase, which the dermal side of the skin tissue is exposed to, from the atmospheric air phase to which the apical side of the epidermis is exposed. A silicon gasket and/or an o-ring may also isolate the temperature and pH sensors and the sample supports from the gas phase. The entire system is placed in a laminar flow hood to maintain sterility and atmospheric air is dependent upon ambient air conditions within the room/laminar flow hood.
Figure 1E:
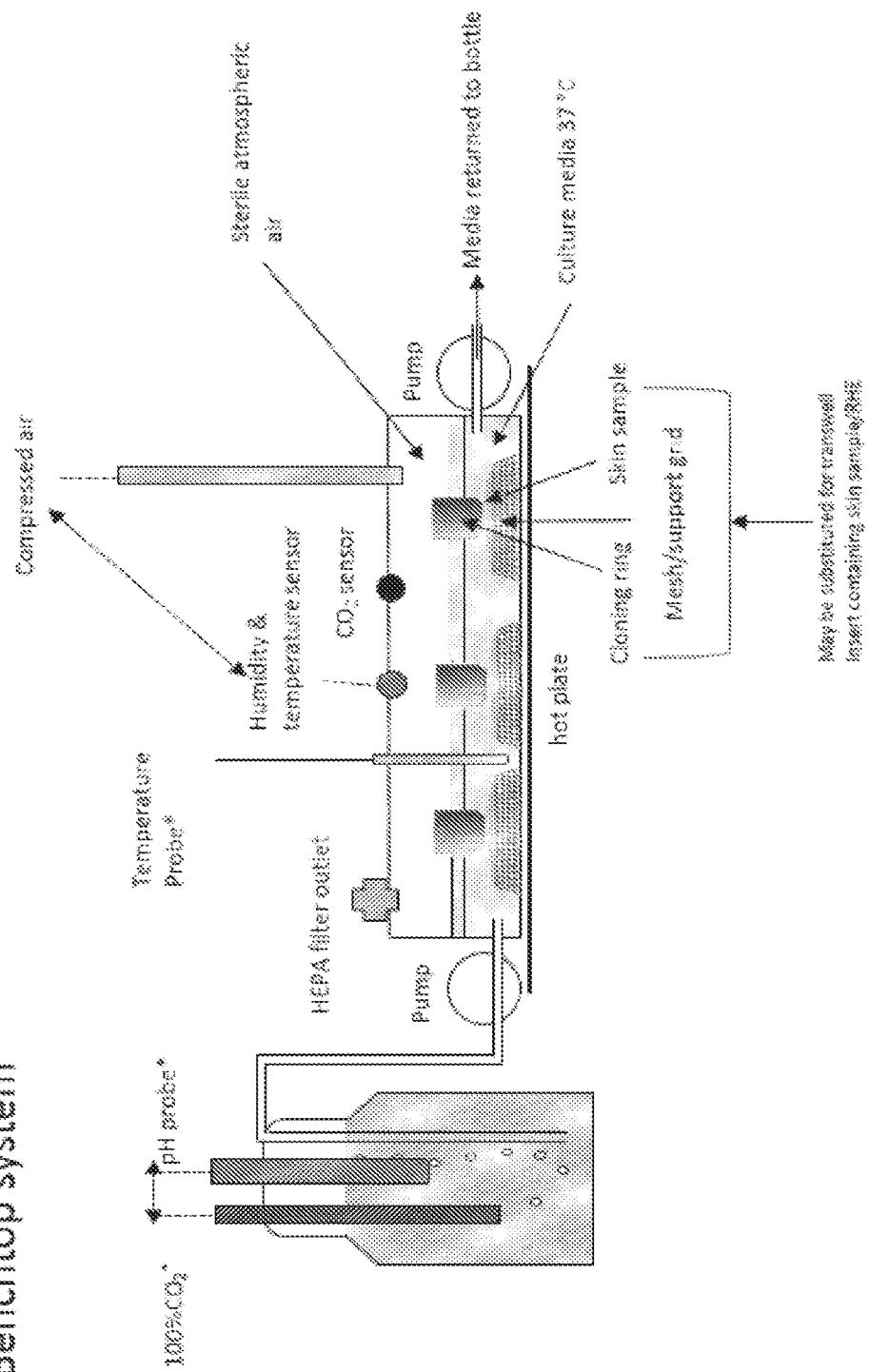
Figure 1F:
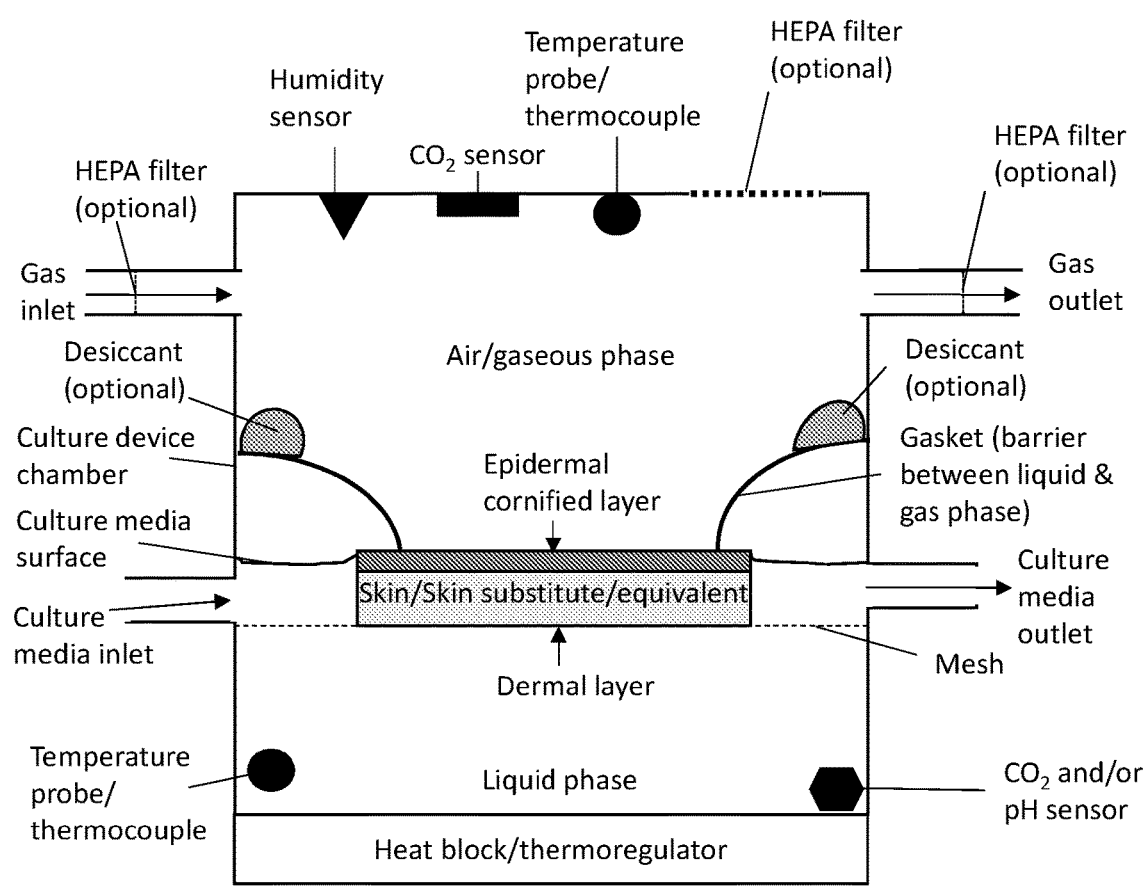
FIG. 1: A skin culturing apparatus configured for biphasic culturing of ex vivo mammalian skin or FT RHE.

FIG. 1F: A benchtop device for maintaining mammalian skin. An autoregulated benchtop device for ex vivo and FT-RHE skin culture with continuous monitoring and feedback control of liquid phase (culture media pH, temperature) and gas phase ($CO_2$, humidity, temperature). The dermis of the skin is exposed to the liquid phase, whereas the majority of the apical side of the epidermal cornified layer is exposed to the gas phase.

The gas phase: optimum skin culture conditions have been determined in experimental analysis as 30-50% RH with $CO_2$ below 1000 ppm (equivalent to 0.1% $CO_2$), with a temperature below 29° C. Gas in the benchtop system is medical air. Gas flow into the gas phase culture chamber is regulated by an on/off valve (for pressurized gas) or a pump, fan and/or vacuum (for non-pressurized gas). HEPA filters ensure that the system remains sterile and provides an outlet to prevent the buildup of pressure. The opening and closing of the gas valve is regulated by relative humidity and/or $CO_2$ through sensors positioned within the gas phase that provide continuous monitoring and feedback control. The gasket provides a seal between the liquid and gas phase to limit fluid loss, humidity buildup, $CO_2$ exchange and temperature exchange between phases.

The liquid phase: optimum skin culture conditions have been determined in experimental analysis as between pH 7.2 and 7.6, 33-37° C. The pH is regulated by linking a pH probe or sensor that continuously monitors culture media pH to a $CO_2$ valve that opens to release $CO_2$ gas into the culture media when the pH is too basic. There is a short burst of gas release, followed by a time delay to allow for the media/$CO_2$/pH to equilibrate to determine the new pH after $CO_2$ release. The system then determines whether the valve needs to open again. If the media pH has been sufficiently buffered, the $CO_2$ valve will remain closed. Alternatively, the culture media pH is regulated by maintaining $CO_2$ levels within the liquid chamber relative to the buffering capacity of the culture media, typically 5-10% $CO_2$. Culture media temperature is regulated at 37° C. (33-37° C.) on a hotplate or heating element with feedback control from the thermal couple positioned in the liquid phase.

Fluidic culture media flow—typically ranging from 0.01 ml/min to 42 ml/min in a closed loop system; but could be single pass/open loop as required, e.g. for culture media sample collection. The liquid level within the device is kept constant at the height of the liquid output by pumping out the media at a higher flow rate than the input flow. The current system is regulated by peristaltic pumps, but any mechanism for mediating fluidic control could be utilized, e.g. syringe/pressure, vacuum, mechanical force. Culture media (defined as any solution that supports the growth and/or viability of mammalian skin) inlet regulated by fluidic control and buffered by $CO_2$ according to detected pH and/or $CO_2$ levels.

Probes/sensors can be positioned anywhere appropriate within the designated gas or liquid phase. Additional probes, sensors, monitoring systems may be integrated into the system to provide analysis on skin function, behavior and biological responses.

Figure 2A:
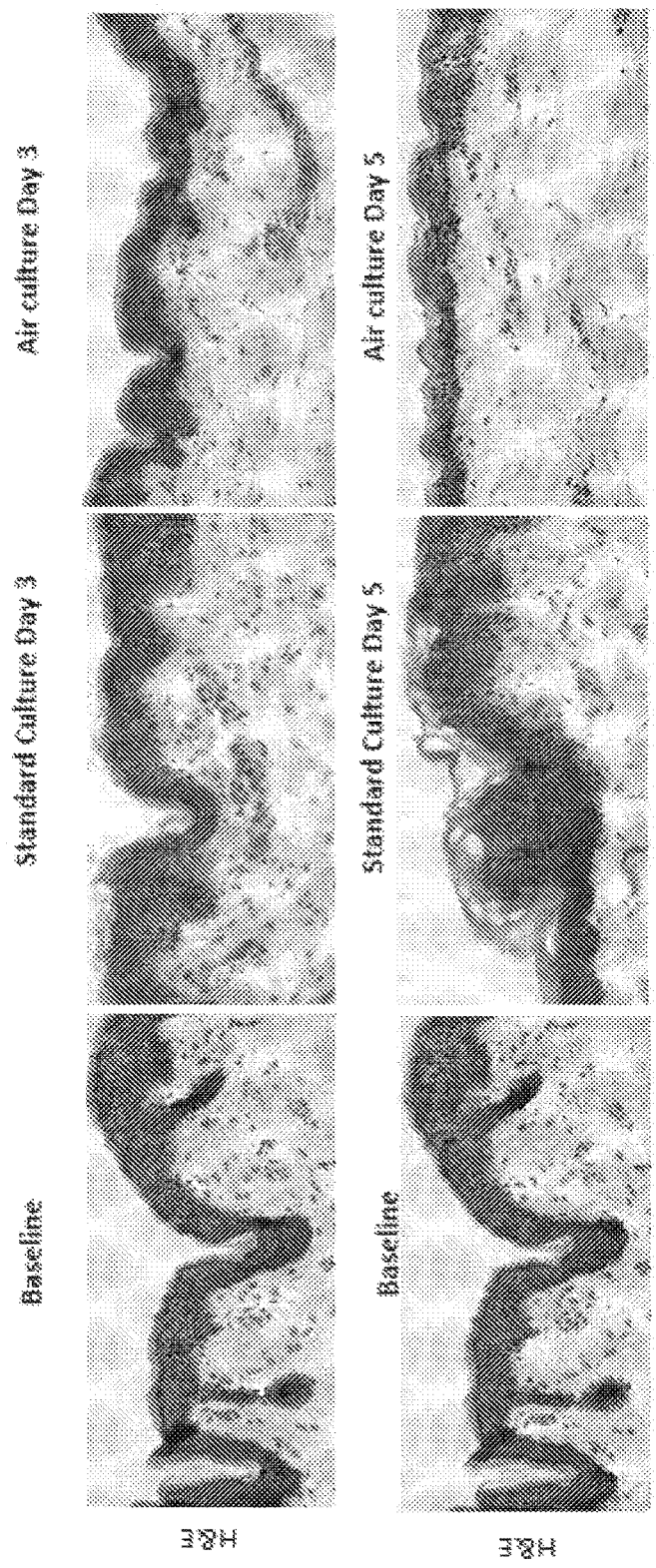
Figure 2B:
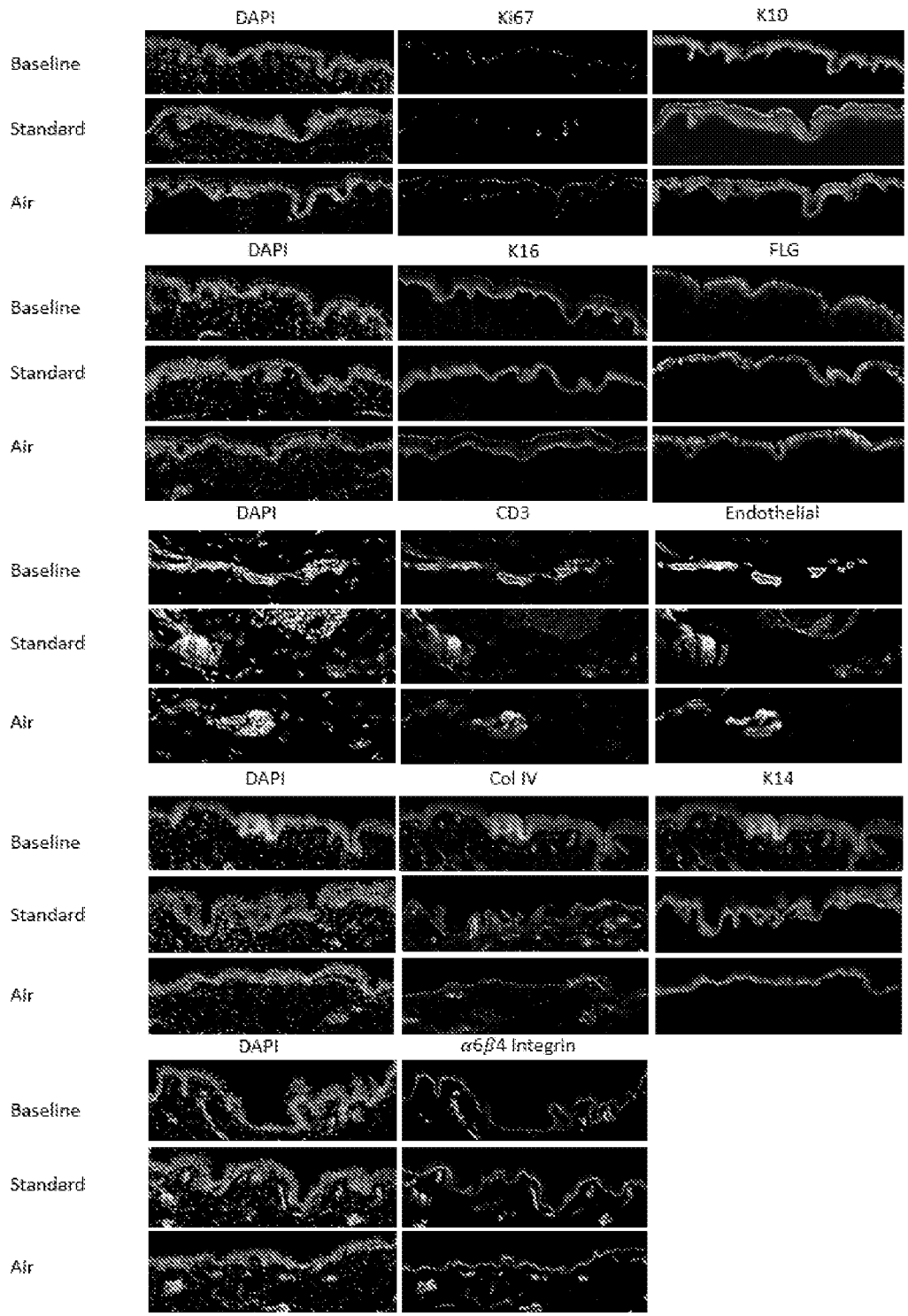
Figure 2C:
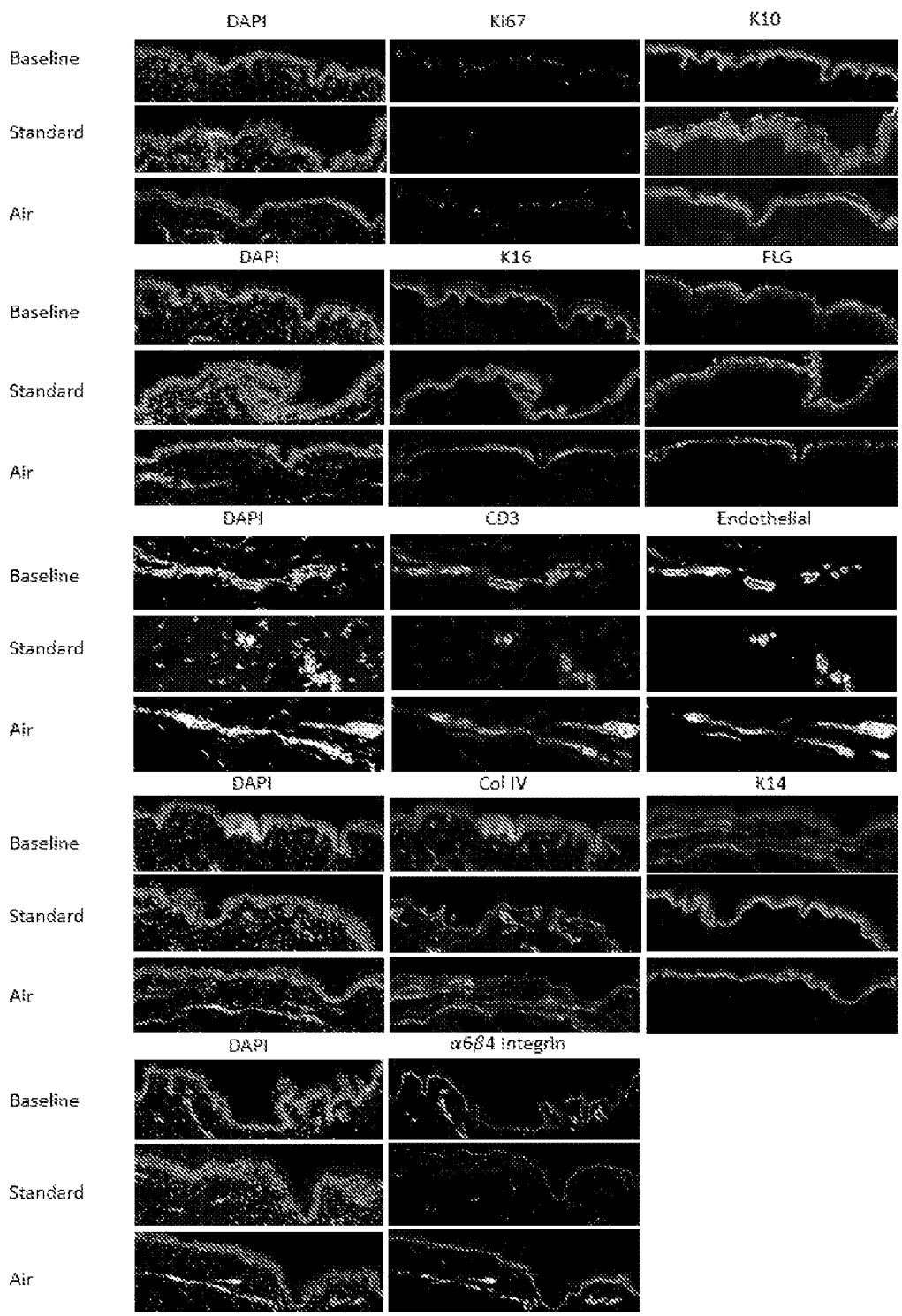

FIG. 2: Hematoxylin and eosin (H&E) and immunofluorescence histochemistry (IFH) of ex vivo skin cultured under air or standard TC conditions. All data was compared to baseline (day 0) skin (freshly isolated skin). FIG. 2A H&E imaging of ex vivo skin at baseline, air culture (day 3 and day 5) and standard TC (day 3 and day 5). FIG. 2B. Differences in ex vivo skin culture from freshly excised skin (baseline) and 3 days of culture using standard (TC incubator) vs. the new skin culture method (air culture, set up as described in FIG. 1B). Tissue samples were analysed by immunofluorescence histochemistry for: Ki67, K10, K16, filaggrin (FLG); CD3+ T cells (green); K14 (red in baseline image), collagen IV (green in baseline image); alpha 6/beta 4 integrin. FIG. 2C. Differences in ex vivo skin culture from freshly excised skin (baseline) and 5 days of culture using standard (TC incubator) vs. the new skin culture method (air culture, set up as described in FIG. 1B). Tissue samples were analysed by immunofluorescence histochemistry for; Ki67, K10, K16, filaggrin (FLG), CD3+ T cells (green); K14 (red in baseline image), collagen IV (green in baseline image); alpha 6/beta 4 integrin.

Figure 3:
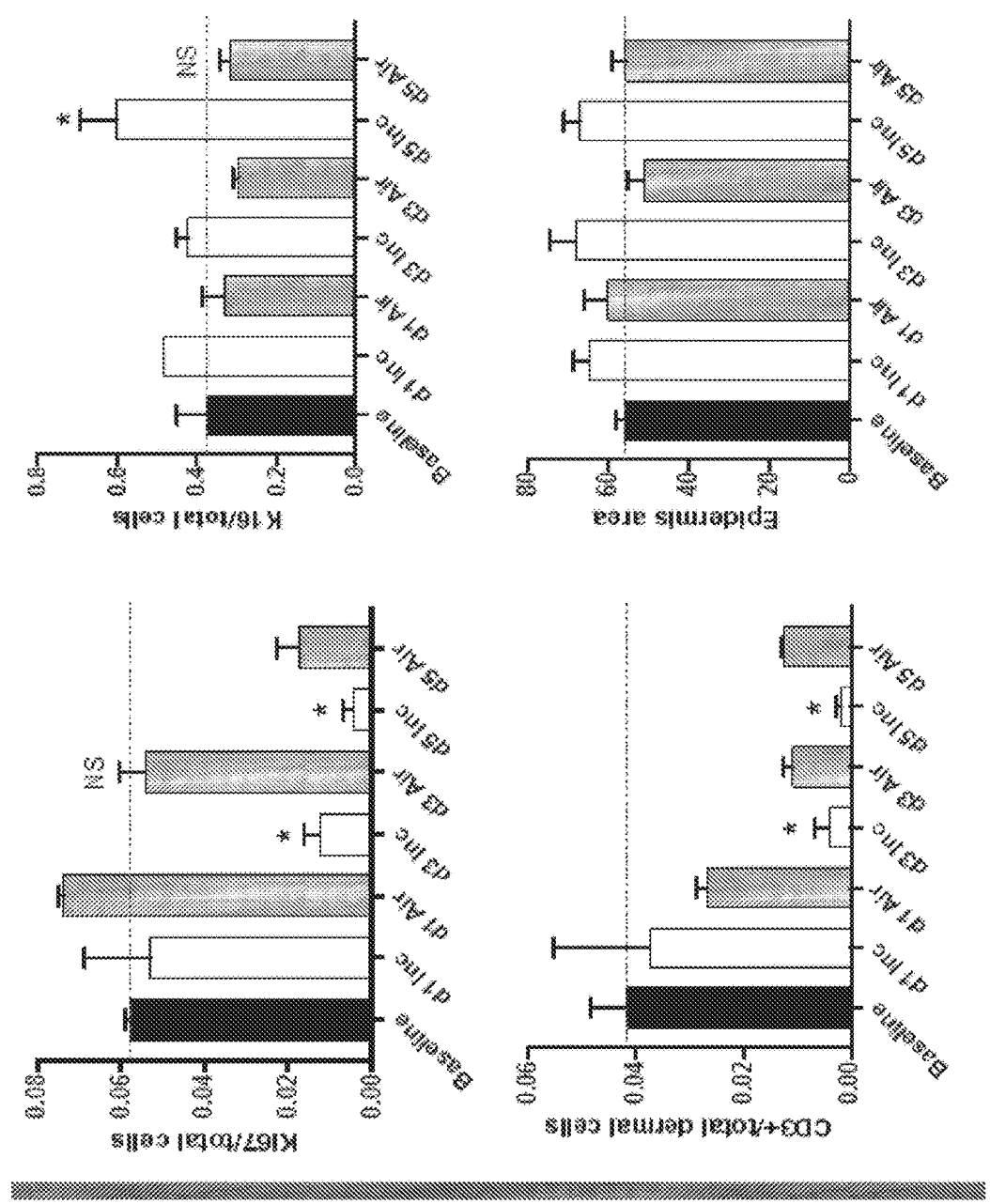

FIG. 3: InCell quantification of immunofluorescent histochemistry data (displayed in FIG. 2) of cell proliferation (Ki67); Hyperproliferation (K16); CD3+ T cells and epidermal thickness.

Figure 4:
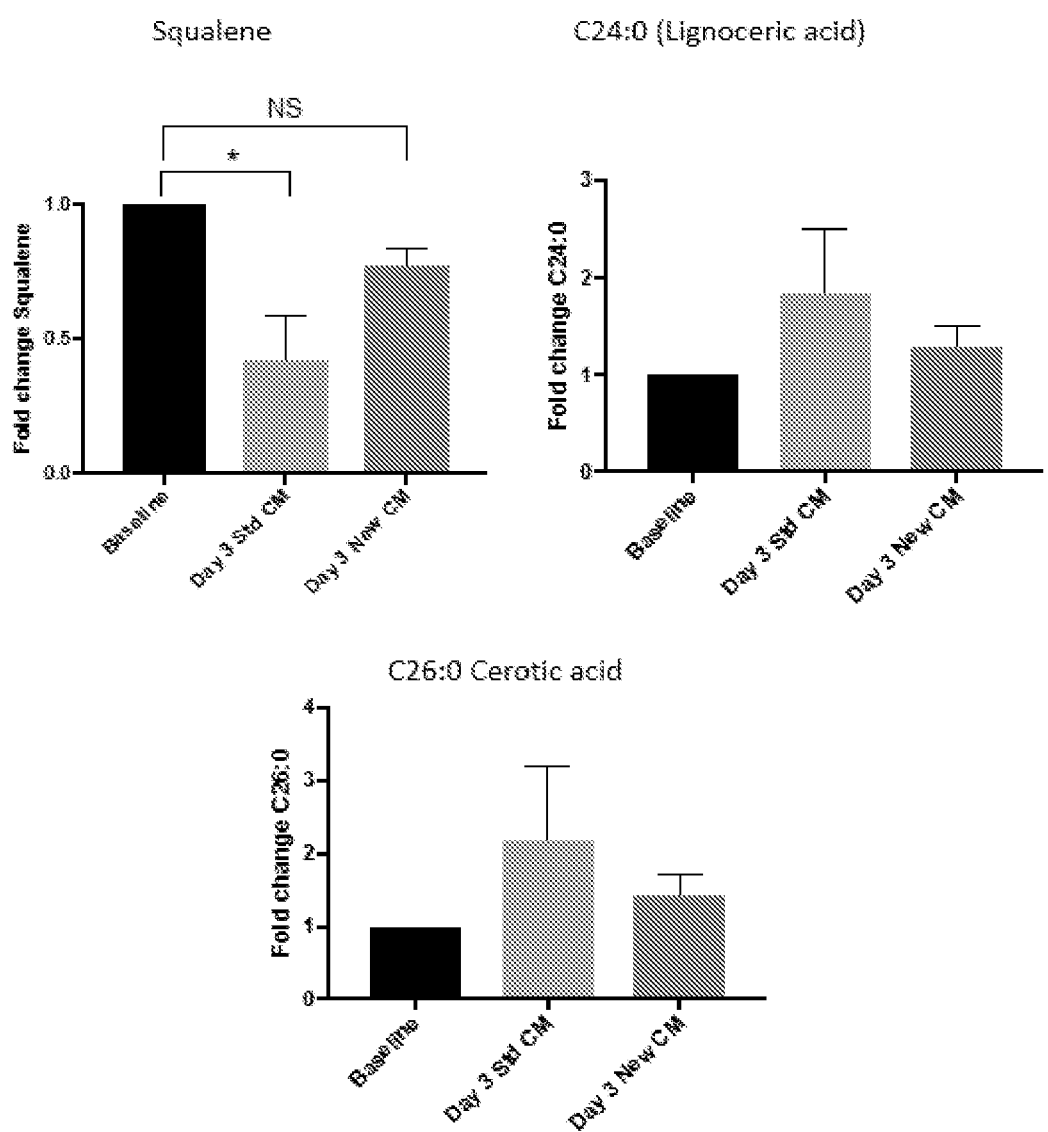

FIG. 4: LC/MS lipid quantification of ex vivo skin cultured under air or standard TC incubator; compared to baseline (day 0) skin.

Figure 5:
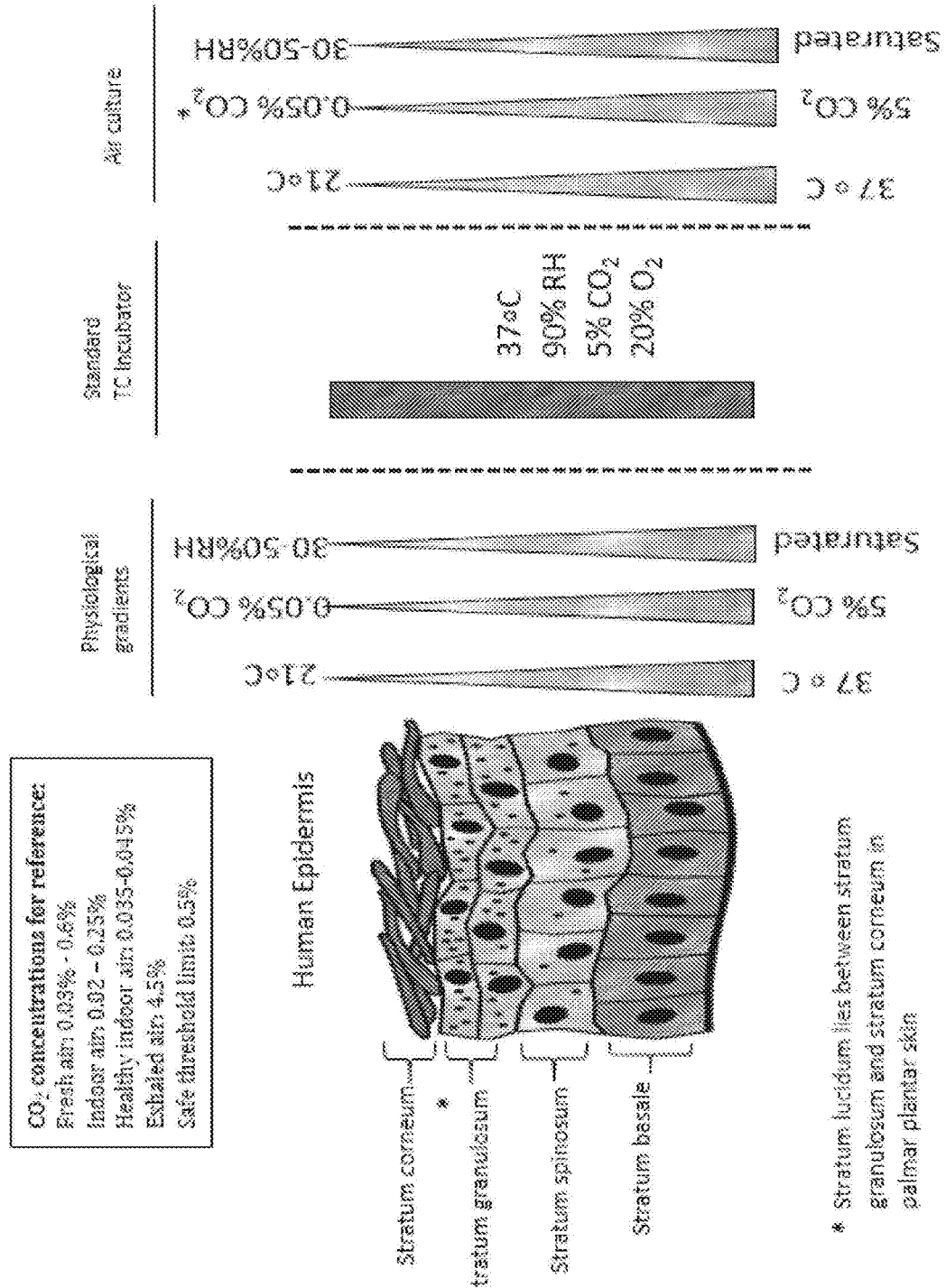

FIG. 5: schematic diagram illustrating the temperature, oxygen, carbon dioxide and relative humidity gradients across the different layers of skin under physiological conditions. No such gradients exist in standard tissue culture incubators, in which the temperature is maintained at 37° C., the relative humidity is maintained at 90%, and the $CO_2$ concentrations are maintained at 5%. In methods according to the present invention, physiologically relevant temperature, $CO_2$ and relative humidity gradients exist across the layers of the skin or skin substitute.

Figure 6:
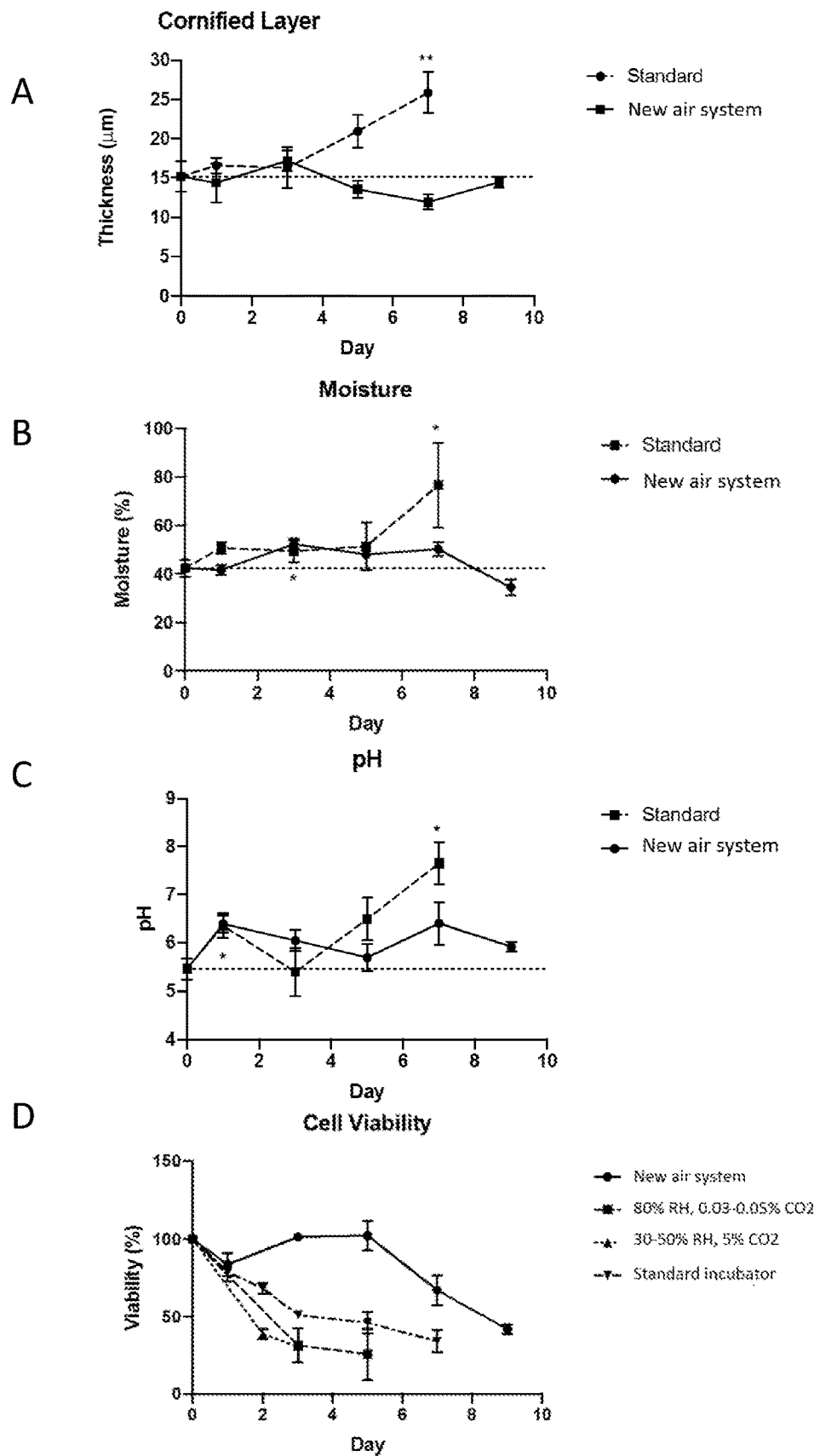

FIG. 6: Skin barrier properties and skin tissue viability using standard (TC incubator) versus the new air system using the benchtop, autoregulated device (as described in FIG. 1F). FIG. 6A: The thickness of the cornified layer was measured from H&E images of tissue sections collected at day 0, 1, 3, 5, 7 (and 9 for the new air culture) after ex vivo skin culture under standard and new air culture conditions.

FIG. 6B: epidermal surface % moisture was measured at day 0, 1, 3, 5, 7 (and 9 for the new air culture) after ex vivo skin culture under standard and new air culture conditions. FIG. 6C: epidermal surface pH was measured at day 0, 1, 3, 5, 7 (and 9 for the new air culture) after ex vivo skin culture under standard and new air culture conditions. FIG. 6D: MTT assay assessing skin tissue metabolism/viability when ex vivo skin was cultured under standard and new air culture conditions. The skin response to additional conditions was assessed to demonstrate the importance of both $CO_2$ levels and RH levels in the air phase culture. Where relevant, statistical analysis for each figure was conducted relative to baseline (day 0 samples) using one-way ANOVA or Tuckey's T-Test, *≤P0.05, **≤P0.01, NS not significant.

DETAILED DESCRIPTION

The inventors have created a novel skin culturing apparatus and method of culturing skin, which addresses many of the failings in existing skin culture models. Fundamentally, ex vivo skin or skin substitutes are cultured in an apparatus comprising two chambers wherein a first surface of the ex vivo mammalian skin or skin substitute is cultured in a gaseous environment, e.g. comprising atmospheric air, rather than in tissue culture medium or exposure to the gaseous environment of standard tissue culture incubators (37° C., 5-10% $CO_2$ and 90-100% relative humidity). This creates a physiologically relevant, native environment specific for skin, which significantly improves or retains normal, healthy skin function compared to standard methods. Moreover, a second surface of the ex vivo mammalian skin or skin substitute is cultured in a tissue culture medium and is not exposed to the gaseous environment.

The apparatus and methods of the invention allow ex vivo skin and skin substitute to be cultured without activation of K16 while retaining normal keratinocyte basal proliferation and differentiation profiles. This indicates that skin cultured in the apparatus retains a normal, healthy keratinocyte profile, instead of activating a partial wounded response. This has never previously been achieved in skin culture. In some embodiments, immune cells are retained in the ex vivo mammalian skin and/or skin substitute following at least five days in culture. This retention of immune cells may indicate that an immune response could also be present that is currently missing from skin models. These data demonstrate that the apparatus of the invention offer a significant advance to skin cell culture, with application to pharmacological, cosmetic and basic research testing.

The gaseous environment may also comprise less than: 5%, 4%, 3%, 2%, 1%, 0.5%, 0.1%, 0.09%, 0.08%, 0.07%, 0.06%, 0.05%, 0.045% or 0.04% $CO_2$. For example, the gaseous environment may comprise 0.02-0.05% or 0.035-0.045% $CO_2$. The gaseous environment may comprise 18-25%, 18-24%, 18-23%, 19-23%, 19-22%, 20-22% or about 21% $O_2$. The gaseous environment may contain about 78% $N_2$, and/or about 1% Argon. The gaseous environment may comprise atmospheric air, compressed air and/or medical air. Medical air may refer to sterile compressed air, and medical air may have a composition of gases that is similar to atmospheric air (e.g. approximately 78% $N_2$ and 21% $O_2$). The gaseous environment may mimic healthy internal room or physiological conditions.

The gaseous environment may have a temperature of below 37° C., e.g. 10-36° C., 12-32° C., 14-29° C., 15-25° C., 18-25° C., 19-24° C., or 20-22° C. The gaseous environment may also have a relative humidity below 90%, e.g. 0-89%, 0-85%, 10-80%, 15-75%, 20-74%, 23-70%, 25-65%, 30-50%, 35-50%, 40-50%, or 40-45%.

The tissue culture medium may be at a temperature of 33.0-37.5° C., e.g. 34-37.5° C., 35-37.5° C., 36-37.5° C. or about 37° C. The tissue culture medium may also be at a pH of 6.1-7.9, e.g. 6.2-7.7, 6.3-7.7, 6.4-7.7, 6.5-7.7, 6.6-7.7, 6.7-7.6, 6.8-7.6, 6.9-7.6, 7-7.6, 7.1-7.6, 7.1-7.5 or 7.2-7.4. The tissue culture medium may comprise 2-10%, 2-8%, 3-7%, 4-6%, or 5% $CO_2$.

The tissue culture medium may comprise Dulbecco's Modified Eagles medium (DMEM), RM+ keratinocyte culture media, EpiLife, KGM Gold keratinocyte growth medium bullet kit, KGM Gold keratinocyte basal medium, KGM-CD Gold keratinocyte growth medium—chemically defined, DMEM:F12; MCDB 153 medium; Keratinocyte SFM, KCM; Clonetics keratinocyte media products; EMEM; William's E medium; and/or a culture medium that supports the growth of keratinocytes and/or dermal fibroblasts. In various embodiments, the tissue culture medium comprises DMEM. The tissue culture medium may comprise 10% (v/v) foetal bovine serum, 1% (v/v) penicillin, 1% (v/v) streptomycin, and/or 1% (v/v) glutamine. In some embodiments, the tissue culture medium comprises 0.6-10, 1-8, 2-6, 3.0-4.5, 3.5-4, or about 3.7 g/mL of sodium bicarbonate.

The skin culturing apparatus is configured for biphasic culturing of ex vivo skin or a mammalian skin substitute. Biphasic culturing may be achieved by providing two chambers: a first chamber comprising a gaseous environment as defined herein, and a second chamber comprising a tissue culture medium, as defined herein, in which a first surface of the ex vivo mammalian skin or skin substitute is exposed to the gaseous environment, but not to the tissue culture medium; and a second surface of the ex vivo mammalian skin or skin substitute is exposed to the tissue culture medium, but not to the gaseous environment. As shown in FIG. 7, biphasic culturing allows for physiologically relevant gradients of temperature, $CO_2$ and relative humidity to be produced across the skin or skin substitute. For example, a second surface of the ex vivo mammalian skin or skin substitute may be exposed to standard tissue culture medium conditions (e.g. having a temperature of approximately 37° C. and/or a $CO_2$ concentration of approximately 5%), whereas a first surface of the ex vivo mammalian skin or skin substitute may be exposed to a gaseous environment having a much lower relative humidity, temperature and $CO_2$ concentration, as defined above. Thus, the apparatus and methods of the invention may facilitate the production of temperature, $CO_2$ and/or relative humidity gradients across the layers of the ex vivo mammalian skin and/or skin substitute housed within the skin sample holder.

The invention may allow the retention of normal, healthy skin function compared to standard methods, e.g. avoiding the activation of K16, retaining normal keratinocyte basal proliferation and differentiation profiles, and/or retaining resident immune cells in ex vivo skin or skin substitutes for longer.

In various embodiments, the cells of the ex vivo mammalian skin and/or skin substitute do not have elevated K16 expression following at least five days in culture relative to baseline levels. Such baseline levels of K16 expression may refer to the K16 expression level immediately prior to culturing in the apparatus of the invention or according to a method of the invention, e.g. at 0 days in culture.

In various embodiments, the gaseous environment is sterile. The term "sterile" as used herein means free or substantially free from bacteria or other living microorganisms. For example, sterile may mean that the apparatus has been cleaned with microsol and/or ethanol.

The term "skin" as used herein may refer to: (1) a barrier that protects internal organs of the body from the external environment, and/or (2) an organ that protects internal organs of the body from chemical, physical, biological, UV assault; and/or (3) an organ that prevents dehydration of the body; and/or (4) an organ that can help regulate body temperature through sweating (to reduce body temperature) or raising hair follicles (to trap air and prevent heat loss) or through altered adipose behaviour; and/or (5) an organ that acts as a cushion against physical trauma to internal organs, muscles, and bones. Skin may comprise an epidermal layer, dermal layer, hypodermal layer; wherein the epidermal layer is subdivided into: (1) a stratum corneum; (2) a stratum granulosum; (3) a stratum spinosum, and (4) a stratum basale. Certain body sites (e.g. palmar-plantar skin) may also contain a stratum lucidum.

As used herein, "healthy skin" may refer to skin that is hydrated, not wounded, and/or substantially disease-free. In some embodiments, the skin provides an intact barrier; and/or normal rates and/or patterns of proliferation and/or differentiation. Proliferating cells may be retained in the basal layer (except palmar plantar skin); and/or the cornified layer remains intact (i.e. not broken). In some embodiments, markers are expressed in the following defined regions: Keratin 1/Keratin 10—all suprabasal layers, Keratin 5/Keratin 14—basal layer, and/or Loricrin—granular and cornified layer.

The epidermal layer primarily consists of keratinocytes but may also comprise melanocytes, Langerhans cells, Merkel cells, stem cells and immune cells; and a cornified layer primarily consisting of proteins and lipids; elements of skin appendages e.g. hair follicle may also traverse the epidermis. The dermal layer may comprise blood vessels; nerves; hair follicles; eccrine sweat glands, sebaceous glands; immune cells, a dermal matrix including dermal fibroblasts and collagen. The subcutis layer (or hypodermis) may comprise adipose tissue, blood vessels, nerves and immune cells.

In various embodiments, the ex vivo mammalian skin is ex vivo rodent (e.g. mouse or rat), rabbit, pig, primate or human skin. The diameter of the ex vivo mammalian skin and/or skin substitute (e.g. that is exposed to the gaseous environment) may be 1-500 mm, 1-400, 1-300, 1-200, 1-100, 1-50, 2-45, 3-40, 4-35, 5-30, 6-25, 7-20, 8-18, 9-16, 10-15, 12-14 or about 13 mm.

As used herein, the term "skin substitute" may refer to a material which possesses anatomical and/or functional similarities with skin. In some embodiments, the skin substitute is a mammalian skin substitute. For example, the skin substitute may be a rodent (e.g. mouse or rat), rabbit, pig, primate or human skin substitute. Skin substitutes include, but are not limited to, bioengineered skin equivalents, tissue-engineered skin, tissue-engineered skin constructs, biological skin substitutes, bioengineered skin substitutes, skin substitute bioconstructs, living skin replacements, dermal-epidermal composites and bioengineered alternative tissue. The skin substitute may: (1) provide a barrier to the external environment, and/or (2) provide protection from chemical, physical, biological, UV assault; and/or (3) prevent dehydration of underlying materials; and/or (4) act as a cushion against physical trauma to underlying materials. A skin substitute may comprise keratinocytes, which may be primary and/or immortalized cells. Said keratinocytes may be reconstructed into a 3D system and/or cultured on a membrane or a dermal matrix.

Recombinant Human Epidermis (RHE) as used herein may refer to: (1) a system in which cultured keratinocytes have been reconstructed into a 3D system to represent human epidermis; and/or (2) a system where keratinocytes (primary or immortalized cells) are cultured in 3D on a membrane. Full Thickness Recombinant Human Epidermis (FT RHE) as used herein may refer to: (1) a system in which cultured skin cells have been reconstructed into a 3D system to represent human skin; and/or (2) a system where keratinocytes (primary or immortalized cells) are cultured above a dermal matrix.

The dermal matrix is typically formed of collagen (but can also be made of other material including hydrogels) and dermal fibroblasts. This combination of keratinocytes and dermal matrix/fibroblasts forms the minimal viable components of a FT-RHE, however other skin cells/combinations of skin cells (e.g. immune cells, melanocytes) can also be included in a FT-RHE. FT-RHE may also be described as 3D organotypic skin/epidermal culture, artificial skin, skin or epidermal equivalent.

A number of companies produce RHE for commercial purposes. These RHE models include Phenion (Henkel), EpiSkin (L'Oreal), EpiDerm (MatTek), epiCS (CellSystems), LabCyte (J-TEC), LabSkin 3D human skin equivalent, and Emulate. In addition, NativeSkin (Genoskin) provide ex vivo human skin for research purposes, and "Skin-on-a-chip" has been developed commercially by TissUse GmbH. Basic fluidic devices for cell culture (e.g. Kirkstall) are available. However, all of the above products are cultured within standard tissue culture incubators. In standard tissue culture incubators, the $CO_2$ concentration is about 5%-10%, the relative humidity is approximately 90-100% and the temperature is 37° C. Moreover, standard tissue culture incubators lack a barrier that separates a first chamber comprising a gaseous environment from a second chamber comprising tissue culture medium.

The 'atmosphere' of air can vary depending on location/weather with temperature and humidity being the greatest variables. The technology described herein is based on the ideal indoor room atmosphere/healthy indoor air quality considered optimum for human health which is specified as follows: humidity—the Environmental Protection Agency states that the ideal relative humidity for human health is 30-60%, but preferably between 40-50%; temperature—room temperature can vary between 15-25° C., but the American dictionary definition of room temperature is preferred at 20-22° C.; $CO_2$—atmospheric $CO_2$ can fluctuate and should be below 1000 ppm but should preferably be between 0.035-0.045%, equivalent to 350-450 ppm and was the range used in this study.

The apparatus may comprise one or more pumps, which may pump tissue culture medium into and/or out of the second chamber. For example, the apparatus may comprise one, two, three, four or more pumps. The pumps may be peristaltic pumps. The flow rate of the tissue culture medium may be 1-200, 1-100, 1-50, 1-45, 1-42, 1-30, 1-20 or 1-10 ml/min. A microcontroller board, such as Ardiuno Uno, may be used to control the $CO_2$ buffering/pH and flow rate through pumps. The tissue culture medium may be maintained at a controlled depth within the second chamber. For example, the tissue culture medium may be maintained at a depth within 5, 4, 3, 2, 1, 0.5 cm of a predetermined depth over the course of 1, 2, 3, 4, 5, 6, 7, 8, 9, 10 days or more of culturing the ex vivo mammalian skin and/or a mammalian skin substitute. The depth may be regulated by the height of a tissue culture medium inlet relative to that of a tissue culture medium outlet and/or by the action of one or more pumps.

The temperature of the tissue culture medium in the second chamber may be maintained by the action of a heater, which may be configured to regulate the temperature of the second chamber, e.g. at 33-37.5° C. In some embodiments, the apparatus comprises a temperature probe, which enables feedback control of the heater in order to maintain the temperature of the tissue culture medium, e.g. at 33-37.5° C., 34-37.5° C., 35-37.5° C., 36-37.5° C., or 36.5-37.5° C. The heater may be a hotplate, heatblock and/or a water bath.

The skin culturing apparatus comprises a barrier, which separates the first and second chambers. The barrier may seal the first chamber from the second chamber, such that a first surface of the ex vivo mammalian skin or skin substitute is exposed to the gaseous environment, but not to the tissue culture medium; and a second surface of the ex vivo mammalian skin or skin substitute is exposed to the tissue culture medium, but not to the gaseous environment. The barrier may be impermeable to the tissue culture medium and/or to the gaseous environment. The barrier may prevent fluid and/or liquid communication between the first and second chambers. The barrier may prevent gas exchange between the first and second chambers. For example, the barrier may prevent the diffusion of $CO_2$ from the tissue culture medium into the gaseous environment.

The barrier may also be configured to receive the skin sample holder. For example, the barrier may comprise one or more orifices configured to house the skin sample holder(s). The barrier may be made from one or more acrylic sheets. The barrier may comprise a means for sealing the first chamber from the second chamber, e.g. to prevent the release of $CO_2$ from the culture medium into the gaseous environment. Said means may be in the form of a gasket, e.g. a silicon gasket, and/or an o-ring.

The skin sample holder is configured to house ex vivo mammalian skin and/or a mammalian skin substitute. The skin sample holder may be received by the barrier. For example, the skin sample holder may be locatable within an orifice in the barrier. The skin sample holder may be configured such that in use a first surface of the ex vivo mammalian skin or skin substitute is exposed to the gaseous environment, but not to the tissue culture medium; and/or a second surface of the ex vivo mammalian skin or skin substitute is exposed to the tissue culture medium, but not to the gaseous environment. In this way, the skin sample holder can facilitate biphasic culturing of skin or skin substitutes. For example, the skin sample holder may be configured such that in use the stratum corneum layer is exposed to the gaseous environment, but not to the tissue culture medium; and/or the stratum basale layer and/or the dermis or dermal equivalent is exposed to the tissue culture medium, but not to the gaseous environment. This may be achieved by controlling the height of the liquid interface and/or positioning the location of the skin sample holder. For instance, a transwell/insert may be positioned such that the bottom of the transwell touches the liquid but the liquid does not overflow/flood the top of the epidermis/epidermal equivalent.

Alternatively, a mesh that ex vivo mammalian skin and/or a mammalian skin substitute sits on and the seal formed by the cloning ring may be positioned such that the stratum corneum layer is exposed to the gaseous environment, but not to the tissue culture medium; and/or the stratum basale layer and/or the dermis or dermal equivalent is exposed to the tissue culture medium, but not to the gaseous environment. In some embodiments, the skin sample or skin equivalent is embedded or surrounded in a gel; and/or has an o-ring on top; and/or is inside a transwell. The gel may be collagen and/or a hydrogel.

The skin sample holder may comprise side walls, and/or it may be in the form of an insert or cup which slots into an orifice in the barrier. In some embodiments, the skin sample holder is a transwell insert or a ring, e.g. a cloning ring. The skin sample holder may comprise a mesh, e.g. a wire mesh, and the ex vivo skin or skin substitute may be locatable on the mesh. In some embodiments, the ex vivo skin or skin substitute is not located on a platform that rests on the base of the second chamber. The skin sample holder may be made of plastic or of metal.

The ex vivo mammalian skin and/or skin substitute may be placed on a liquid-permeable base, e.g. a wire mesh or plastic containing pores. In this configuration, a second surface of the ex vivo mammalian skin or skin substitute may be placed on the liquid-permeable base, such that in use the second surface of the ex vivo mammalian skin or skin substitute is exposed to the tissue culture medium.

The apparatus may lack a housing, i.e. such that the first chamber is exposed to the surrounding environment. The apparatus may be located in a laminar flow hood in order to maintain sterility. An atmospheric monitor may be used to monitor the conditions in the gaseous environment.

Alternatively, the apparatus may comprise a housing that encloses the first and second chambers. The housing may prevent exposure of the first chamber to the surrounding environment, e.g. such that the apparatus can be used outside a laminar flow hood. Thus, the apparatus may be a closed system, which may provide stable and/or consistent conditions for the culturing of ex vivo mammalian skin and/or a mammalian skin substitute. In such an apparatus, fluctuations in temperature, humidity and/or gaseous composition may be reduced relative to an apparatus in which the first chamber is exposed to the surrounding environment. The apparatus may also comprise an inflow pipe which is configured to deliver gases into the first chamber. The gases may constitute the gaseous environment. In various embodiments, said gases are atmospheric air, compressed air, and/or compressed medical air. The housing may comprise a filter outlet, e.g. a HEPA filter outlet. The filter outlet may be configured to enable the release of gases, e.g. to prevent the build-up of pressure, whilst maintaining sterility within the apparatus.

The apparatus may also comprise one or more pH probe(s), temperature probe(s), $CO_2$ sensor(s), and/or humidity sensor(s). For example, the first chamber may comprise a $CO_2$ sensor, a humidity sensor and/or a temperature probe to monitor the conditions in the gaseous environment. The apparatus may comprise a temperature probe and/or pH sensor in the second chamber to monitor the conditions in the tissue culture medium, wherein optionally said sensors are exposed to the tissue culture medium, but not the gaseous environment. For example, a silicon gasket and/or an o-ring may isolate the temperature and/or pH sensors from the gaseous environment. Gaseous environment and tissue culture medium temperatures, $CO_2$ level, humidity and/or pH over time may be recorded for further analysis. In some embodiments, the pH probe(s), temperature probe(s), $CO_2$ sensor(s), and/or humidity sensor(s) send readings to a computer or mobile phone application. Sensors in the gaseous environment and/or tissue culture medium and controls may be removed to simplify the operation in environments where these parameters are already controllable or known, i.e. an incubator.

The apparatus may provide monitoring and feedback control of the gaseous environment and/or tissue culture medium in order to maintain the conditions within the gaseous environment and/or tissue culture medium. Said monitoring and/or feedback control may be continuous or at short time intervals (e.g. every 10 minutes, 5 minutes, 1 minute, 30 seconds, 20 seconds, 10 seconds, or 5 seconds). For example, if a condition (e.g. $CO_2$ concentration, relative humidity, pH and/or temperature) exceeds a threshold value, the apparatus may be configured to bring the condition back down below the threshold value. For example, the apparatus may comprise a pH probe in the tissue culture medium, wherein, when the pH exceeds a threshold value, a valve is opened which allows the inflow of $CO_2$ into the tissue culture medium in order to reduce the pH of the tissue culture medium. When the pH of the tissue culture medium subsequently drops below a threshold value, the valve may be closed to prevent any further reduction in the pH of the tissue culture medium. Similarly, the apparatus may comprise a humidity probe in the gaseous environment, wherein, when the humidity exceeds a threshold value, a valve is opened which allows the inflow of compressed air into the tissue culture medium in order to reduce the humidity in the gaseous environment. When the humidity of the gaseous environment subsequently drops below a threshold value, the valve may be closed to prevent any further reduction in the humidity of the gaseous environment.

The apparatus may comprise a $CO_2$ supply and an openable closure, e.g. a valve. The openable closure may open to allow the inflow of $CO_2$ into the tissue culture medium, e.g. when the pH of the tissue culture medium exceeds a threshold pH.

The apparatus and/or methods of the invention may enable the ex vivo mammalian skin and/or skin substitute to retain a normal barrier, lipid profile of epidermal cells, proliferation and/or retention of immune cells for at least 3 days.

In various embodiments, the cells of the ex vivo mammalian skin and/or skin substitute do not have elevated K16 expression (K16 being a marker of hyperproliferation that is induced upon skin wounding) following at least five days in culture relative to baseline levels. This observation has not been observed in prior art keratinocyte cell culture methods. Thus, the apparatus and methods of the invention may enable the retention of normal, rather than partial wounded or hyperproliferative, physiological behaviour of healthy keratinocytes. Such baseline levels of K16 expression may refer to the K16 expression level immediately prior to culturing in the apparatus of the invention or according to a method of the invention, e.g. at 0 days in culture, for any given sample of ex vivo mammalian skin and/or skin substitute.

Epidermal cells of the ex vivo mammalian skin and/or skin substitute may retain a normal lipid profile following at least three days in culture. For example, in some embodiments, the lipid profile is not substantially different from the baseline reading. Such a baseline reading may refer to the lipid profile immediately prior to culturing in the apparatus of the invention or according to a method of the invention, e.g. at 0 days in culture, for any given sample of ex vivo mammalian skin and/or skin substitute. For example, the level of each lipid type may be within ±50%, 40%, 30%, 25%, 20%, or 15% of its level at day 0. The lipid profile may refer to the abundance of C12:0, C13:0, C14:0, 13Me-C15:0, C15:0, 12 Me-C15:0, C16:1, C16:0, 15 Me-C17:0, 14Me-C17:0, C18:2, C18:0, C19:0, C20:1, C20:0, C21:0, C22:0, C23:0, C24:0, C25:0, C26:0, Squalene, Vitamin E, Cholesterol, and/or C14:1. In various embodiments, the abundance of squalene (and/or any of the aforementioned lipids) in epidermal cells of the ex vivo mammalian skin and/or skin substitute may be maintained at baseline levels or substantially close to baseline levels (e.g. within ±50%, 40%, 30%, 25%, 20%, or 15% of baseline levels) following three days in culture.

In various embodiments, the cells of the ex vivo mammalian skin and/or skin substitute express keratinocyte differentiation markers at normal detectible levels following at least five days in culture, e.g. relative to baseline levels. Thus, in some embodiments, the expression levels of keratinocyte differentiation markers are not substantially different from baseline expression levels. Such a baseline reading may refer to the expression levels of keratinocyte differentiation markers immediately prior to culturing in the apparatus of the invention or according to a method of the invention, e.g. at 0 days in culture, for any given sample of ex vivo mammalian skin and/or skin substitute. For example, the level of each keratinocyte differentiation marker may be within ±50%, 40%, 30%, 25%, 20%, or 15% of its level at day 0.

The invention also provides a method of culturing ex vivo mammalian skin and/or a mammalian skin substitute, said method comprising maintaining a first surface of the ex vivo mammalian skin or skin substitute in a gaseous environment comprising less than 5% $CO_2$, at a temperature below 37° C. and a relative humidity below 90%; and maintaining a second surface of the ex vivo mammalian skin or skin substitute in a tissue culture medium at a temperature of 33.0-37.5° C. and pH of 6.1-7.9; wherein the first surface of the ex vivo mammalian skin or skin substitute is not exposed to the tissue culture medium; and the second surface of the ex vivo mammalian skin or skin substitute is not exposed to the gaseous environment.

The first and second surfaces of the ex vivo mammalian skin or skin substitute may be maintained in the gaseous environment and tissue culture media, respectively, for 1-15, 1-13, 1-11, 1-9, 1-7, 1-5, 2-14, 2-12, 2-10, 2-8, 2-6, 3-13, 3-11, 3-9 or 3-7 days.

The invention also provides methods for assessing the genomic, transcriptomic, metabolomic, lipidomic and/or proteomic response of skin or a mammalian skin substitute. Such methods may be applied to skin cells, immune cells, keratinocytes, and/or dermal cells. For example, such methods may be used to determine changes in gene expression in skin cells, immune cells, keratinocytes, and/or dermal cells.

All of the testing methods of the invention (e.g. the above-described methods for testing the effect of a compound or composition; assessing barrier function; assessing immune function and/or inflammation; assessing genomic, transcriptomic, metabolomic, lipidomic and/or proteomic response; assessing dermal absorption; assessing skin sensitization and/or skin irritation; and testing the effect of a gas, aerosol or pollutant) may be applied to ex vivo mammalian skin and/or a mammalian skin substitute which has been cultured according to the invention. In some embodiments, these methods do not comprise an active step of culturing the ex vivo mammalian skin and/or a mammalian skin substitute.

EXAMPLES

Example 1

Skin Specimens: Normal human skin specimens were obtained with informed consent during routine aesthetic surgery. The East London and City Health Authority Research Ethics Committee approved the use of redundant human skin (LREC No. 09/H0704/69).

A skin culturing apparatus configured for biphasic culturing of ex vivo mammalian skin or FT RHE (FIG. 1) was created to maintain a fluidic, biphasic skin culture system where the basal side dermal side of the skin or RHE is fully immersed in culture media regulated at 37° C., pH 7.2-7.4 (controlled by $CO_2$ gas buffering); and the apical side of the epidermis/RHE is exposed to sterile atmospheric air (18-23° C., 0.03-0.05% $CO_2$, 30-50% RH (relative humidity). The device is controlled by an Ardiuno Uno (RS Systems) that regulates $CO_2$ buffering/pH and flow rate through peristaltic pumps, the culture device tank, which contains ex vivo skin or FT RHE samples, sits on a heatblock to regulate an internal chamber culture media temperature at 33-37° C. The whole system sits within a laminar flow hood to maintain sterility.

Ex vivo human skin culture: Skin was prepared by removing adipose tissue and cutting into 2 $cm^2$ pieces. Skin was placed on top of a wire mesh dermis side down, allowing tissue culture medium (Dulbecco's Modified Eagles medium, DMEM containing 10% (v/v) foetal bovine serum, 1% (v/v) penicillin, 1% (v/v) streptomycin, 1% (v/v) glutamine) to flow under the skin specimens, and placed in the tank of the device. A stainless steel cloning ring (130 mm internal diameter) was placed on top of each skin sample to form a seal between the edge of skin, the culture medium and atmospheric air. A plastic insert with silicone gasket sealed the basal fluidic system from the apical atmospheric air environment. An additional simple fluidic system without biphasic culture control (i.e. only with culture media flow) was set up in a standard tissue culture incubator (5% $CO_2$, 37° C., 90-100% RH) to provide a direct comparison between standard culture methods and the new atmospheric air culture method. Time 0 skin samples were collected at the point of delivery to provide a baseline reading of all assays to identify the specific skin physiology that needed to be maintained throughout culture specific to each donor.

Example 2

Immuofluorescence histochemistry: Frozen 5 μm sections of skin were thawed for 20 min at room temperature then fixed and permeabilised in ice-cold 1:1 (v/v) methanol: acetone (Sigma-Aldrich, Poole, UK) for 10 min at −20° C. All tissue sections were blocked in 3% (v/v) donkey serum (Sigma-Aldrich, Poole, UK) for 1 h at room temperature. Negative controls consisted of sections incubated with non-immune serum, PBS-Tween 20 with 3% (v/v) donkey serum (Sigma-Aldrich, Poole, United Kingdom), in place of primary antibody. All other sections were incubated overnight at 4° C. with primary antibodies and 3% (v/v) donkey serum. Primary antibody binding was detected by applying Alexa Fluor 488, 547, 608 against relevant host IgG (each at 2 m/ml) for 1 h at room temperature. The DNA-binding dye 4',6-diamidino-2-phenylindole dihydrochloride (DAPI, Sigma-Aldrich, Poole, United Kingdom) was used to visualise the cell nuclei in skin sections. Sections were mounted using immunofluorescent mounting medium (DakoCytomation, Glostrup, Denmark). Fluorescent images were acquired on a INCA2200 (GE) automated microscope and quantitatively analysed using Developer Toolbox (GE v 1.9.2).

Lipid analysis: Epidermis was separated from a small portion of skin (approx. 6 $mm^2$) at day 0 and day 3 by immersing in dispase II (Sigma-Alridch, Poole, UK) for 45 mins at 37° C. The epidermis was collected in triplicate for each biopsy and time point, washed three times in PBS, dried and weighed. Lipid content was analysed by GC/MS and LC/MS.

Example 3

FT RHE culture: Phenion FT RHE (Henkel) and/or Epiderm (MatTek) and/or Native Skin® (Genoskin) are in culture for 1, 2, 3, 4, 5 6 or 7 days in the air tank. Corresponding FT RHE/Native Skin® are in a standard tissue culture incubator (in a corresponding fluidic device) for direct comparison between the two culture methods. Additional FT RHE samples and/or Native Skin® are also in culture according to the suppliers protocol to provide comparative examples of standard methods to the air device. All FT RHE and/or Native Skin® are in culture using the culture media provided by the supplier. FT RHE and/or Native Skin® are also compared to freshly isolated human skin tissue to examine whether normal skin physiology is retained.

Barrier function is assessed by adding 1 mM lucifer yellow to the upper surface of the epidermis for 6 and/or 24 h. The skin sample is embedded in OCT and cut to 5 μm sections. Imaging of Lucifer yellow transverse into skin sections is collected at 488 nm wavelength and quantified with InCell 2200 analysis.

Results

Basic physiology of ex vivo skin cultured in the new air system (FIG. 1) was compared against an equivalent device under standard culture conditions, i.e. an identical fluidic device, matching the same configuration as the air (benchtop device [FIG. 1C and FIG. 1E] or laminar flow hood device [FIG. 1B and FIG. 1D]), but where the atmosphere and media pH is regulated by the tissue culture incubator environment (e.g., 5% $CO_2$, 37° C., 90-100% RH), sterility is maintained with a lid containing a HEPA filter for gas exchange. This is because inclusion of fluidics alone can improve cell culture and the dimensions/configuration of the apparatus could influence skin physiology. This set up allows us to distinguish the difference of atmospheric culture vs. the standard tissue culture environment. All culture samples were also compared to day 0, i.e. freshly isolated skin tissue from the same donor, representing the ideal physiological baseline function aiming to be retained in culture. FT RHE made with primary human dermal fibroblasts and immortalized NEB1 keratinocytes were also constructed and tested in the air new system against standard culture. Outputs of cell proliferation, differentiation, barrier function and immune cell retention were tested.

H&E analysis in FIG. 2A showed regions of the cornified layer of ex vivo skin begin to fragment at day 3 under standard methods but retained a discrete layer, similar to day 0 with the new air culture method. By day 5 (FIG. 2A), the cornified layer of ex vivo skin was entirely separated and disrupted under standard methods but retained a compact, discrete layer, similar to day 0 with the new air method. At day 5, the entire epidermis also appeared to be thicker with enlarged cells under standard culture methods compared to air day 5 and day 0 samples. Measurements of epidermal thickness verified that the overall thickness significantly increased with standard culture methods but retained normal epidermal thickness in air culture at day 3 and 5. There was no significant difference in epidermal thickness between day 3 and day 5 air samples compared to day 0, indicating the baseline thickness of the epidermis is better maintained under air culture conditions.

Cell proliferation was quantified from IFH staining of Ki67 (FIG. 2B, FIG. 2C and FIG. 3). There was no change in the number of Ki67 positive cells in ex vivo skin between baseline and day 3 air cultures. In contrast, there was a significant reduction in the number of Ki67+ cells by day three under standard culture methods. By day 5 there were almost no detectable Ki67+ cells in standard culture but some Ki67+ cells were still retained using air culture, albeit at a reduced number. This demonstrates that air culture was able to retain normal cell proliferation for longer, at least 3 days, in the epidermis of ex vivo cultured skin. It also suggests that increased epidermal thickness observed from day 3 of standard culture, was likely due to tissue oedema rather than hyperproliferation.

Activation of K16 in cell culture has been a persistent detrimental problem of standard skin tissue and keratinocyte cell culture. In vivo, K16 is only elevated in normal palmar-plantar skin, during wound healing and in hyperproliferative skin conditions such as psoriasis. Thus the observed activation of K16 during standard culture is consistent with the semi-wounded skin cell state reported to occur when skin and skin cells are removed from the body and cultured in vitro. Remarkably, K16 was not elevated in ex vivo skin culture under air throughout the 5 day time course but was significantly elevated by day 5 using standard culture methods (FIG. 2C & FIG. 3).

Culturing ex vivo skin in atmospheric air was also able to better retain resident immune skin cells. Quantitative IFH demonstrated a significant loss of CD3+ cells from day 3 and day 5 under standard cell culture (FIG. 2B, FIG. 2C & FIG. 3). In contrast, a significant retention of resident immune cells was observed in air culture of CD3+ cells by IFH at day 3 and 5 (FIG. 2B, FIG. 2C & FIG. 3).

Healthy keratinocyte differentiation is essential for correct formation of the epidermal stratum corneum and thus barrier function. Keratin 10 (K10) represents and early differentiation marker and Filaggrin (FLG) is a late differentiation marker. K10 and FLG were well retained in both air and incubator culture methods, though there was clear disruption in the expression profiled of K10 and FLG in the cornified layer of ex vivo skin at day 5 standard culture (FIG. 2C), consistent with H&E observations (FIG. 2A). In contrast, discrete K10 and FLG profiles were maintained in ex vivo skin under air culture similar to baseline patterning (FIG. 2C).

In addition to protein differentiation profiles, epidermal lipids are essential for skin barrier maintenance. Although protein differentiation markers of standard cultured ex vivo skin and RHE are faithful to in vivo skin, lipid ratios fail to be correctly maintained in culture. Using LC/MS, squalene was maintained in ex vivo skin at baseline levels with air culture but significantly reduced with standard culture. C24:0 (lignoceric acid) and C26:0 (cerotic acid) exhibited an elevated trend in standard culture but was closer to baseline levels with air culture (FIG. 4).

Basement membrane proteins a6134 integrin and collagen 4 that connect the epidermis to the dermis were well maintained in all ex vivo culture samples including day 5 of both air and standard ex vivo skin culture (FIG. 2C).

Example 4

Skin Specimens: were obtained and cultured as per example 1, with the exception that the culturing apparatus was a benchtop system (as in FIG. 1F), where both the liquid phase and gas phase are continuously monitored and automatically regulated so that the liquid phase conditions are maintained at 37° C., pH 7.2-7.4 and the air/gas phase conditions are maintained at 30-50% RH and 0.03-0.05% $CO_2$.

Ex vivo human skin culture: Skin was prepared as in example 1, with the exception that a lid was placed on top of the apparatus that included: a HEPA filter, $CO_2$ monitor, gas inlet and outlet with gas (medical air/atmospheric air), RH monitor (as shown in FIG. 1F). Tissue metabolism/viability: Skin samples were measured by MTT assay to assess whether cells within the skin samples were metabolically active and therefore viable. Small (10 mg-60 mg) skin pieces were collected in triplicate on day 0 and up to day 10, weighed and cut into smaller pieces. The skin samples were immersed in 0.5 mg/ml Thiazolyl Blue Tetrazolium Blue (MTT) solution for 2 hours at 37° C., 5% $CO_2$, then washed three times in PBS and immersed in 0.4 ml isopropanol overnight. The samples were vortexed, 2× 175 ul of the isopropanol fraction was transferred to a 96 well plate and colorimetric absorbance was measured at 570 nm.

Skin Barrier properties: Skin moisture was measured using SKIV Digital Skin Moisture Detector (Sonew) probe, skin surface pH was measured using pH electrode InLab Surface probe (Mettler Toledo). The thickness of the cornified layer was assessed by measuring the thickness of the cornified layer using Image J analysis on images of H&E stained skin sections.

Results

The primary function of human skin, skin samples were assessed for epidermal percentage moisture, surface pH and cornified layer thickness (measured by Image J from H&E images). Under standard culture conditions, epidermal thickness significantly increased from day 0 baseline from day 5 onward. By day 7, surface pH, percentage moisture and cornified layer had significantly increased from baseline under standard culture conditions. In contrast, surface pH, percentage moisture and cornified layer thickness were effectively maintained at baseline (day 0) levels for at least 7 days using the new air system (FIG. 6).

The ability to maintain tissue viability and metabolism is critical for maintaining skin cell function. MTT assay was used to assess whether skin tissue was metabolically active (and therefore viable) after culture in both standard and the new air system. Additional analysis was developed to demonstrate the critical interdependence of both $CO_2$ and humidity for regulating skin tissue viability. FIG. 6D shows that compared to standard culture $CO_2$ incubator method, skin could be maintained above 90% tissue viability relative to day 0 for at least 5 days. In contrast, tissue viability steadily decreased from day 1 under all culture conditions (e.g. where the gas phase $CO_2$ and/or humidity is high) other than the new air system (where $CO_2$ was 0.03-0.05% and RH was 30-50%). This demonstrates that both the correct $CO_2$ level and the correct humidity level are important for maintaining the metabolic profile of mammalian skin.

Example 5

Skin Specimens: were collected as per example 1.

A skin culturing apparatus configured with varied $CO_2$ and humidity levels to the apical side of human skin was created to demonstrate the linked importance of $CO_2$ and humidity for maintaining ex vivo mammalian skin or FT RHE (FIG. 1F). A fluidic, biphasic skin culture system where the basal side dermal side of the skin or RHE is fully immersed in culture media regulated at 37° C., pH 7.2-7.4 (controlled by $CO_2$ gas buffering); and the apical side of the epidermis/RHE is exposed to (a) sterile medical air 0.03-0.05% $CO_2$, 30-50% RH; or (b) 80% RH, 0.03-0.05% $CO_2$; or (c) 30%-50% RH, 5% $CO_2$; or (d) 90-100% RH and 5% $CO_2$. The device is controlled by an Ardiuno Uno (RS Systems) that regulates $CO_2$ buffering/pH and flow rate through peristaltic pumps, the culture device tank, which contains ex vivo skin or FT RHE samples, sits on a heatblock to regulate an internal chamber culture media temperature at 33-37° C. The gas phase was also regulated by an Ardiuno Uno (RS Systems) that controlled the opening and closing of valves linked to air/gas exchange to maintain the desired RH level. $CO_2$ levels were maintained by purchasing gas canisters containing 5% $CO_2$ or medical air.

Ex vivo human skin culture: Skin was prepared as described in Example 1.

Tissue metabolism/viability: Skin samples were measured by MTT assay to assess whether cells within the skin samples were metabolically active and therefore viable. Small (10 mg-60 mg) skin pieces were collected in triplicate on day 0 and up to day 10, weighed and cut into smaller pieces. The skin samples were immersed in 0.5 mg/ml MTT solution for 2 hours at 37° C., 5% $CO_2$, then washed three times in PBS and immersed in 0.4 ml isopropanol overnight. The samples were vortexed, 2× 175 ul of the isopropanol fraction was transferred to a 96 well plate and colorimetric absorbance was measured at 570 nm.

Example 6

Skin Specimens: are collected as per example 1.

A skin culturing apparatus is configured with an air phase of 0.03-0.05% $CO_2$, 30-50% RH to the apical side of human skin; and where the basal side dermal side of the skin or RHE is fully immersed in culture media regulated at 37° C., pH 7.2-7.4 (controlled by $CO_2$ gas buffering) and 0.2-15% O2 (controlled by continuous monitoring and feedback analysis with $O_2$ sensors housed in the culture media; to lower $O_2$ saturation in liquid phase chamber and/or culture media vessel below 21% atmospheric levels, a vacuum is applied to the media and extracted air/gases is replaced with 0.2-15% $O_2$ balanced with argon and/or nitrogen and/or $CO_2$).

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

Although the foregoing invention has been described in some detail by way of illustration and example for purposes of clarity of understanding, it will be apparent to those skilled in the art that certain minor changes and modifications will be practised. Therefore, the description and examples should not be construed as limiting the scope of the invention, which is delineated by the appended claims.

The invention claimed is:

1. A skin culturing apparatus configured for biphasic culturing of ex vivo mammalian skin or a mammalian skin substitute comprising a first chamber, a second chamber, a barrier, and a skin sample holder, wherein:

the first chamber is configured to provide a gaseous environment having a relative humidity below 90% and comprising less than 5% $CO_2$;
the second chamber is configured to provide tissue culture medium at a temperature of 33.0-37.5° C. and pH of 6.1-7.9;
the skin sample holder is configured to house ex vivo mammalian skin and/or a mammalian skin substitute; and
the barrier separates the first and second chambers, and is configured to receive the skin sample holder;
wherein in use:
(i) the first chamber comprises a gaseous environment having a relative humidity below 90% and comprising less than 5% $CO_2$;
(ii) the second chamber comprises a tissue culture medium at a temperature of 33.0-37.5° C. and pH of 6.1-7.9;
(iii) the skin sample holder houses ex vivo mammalian skin and/or a mammalian skin substitute;
(iv) a first surface of the ex vivo mammalian skin and/or skin substitute is exposed to the gaseous environment, but not to the tissue culture medium; and
(v) a second surface of the ex vivo mammalian skin and/or skin substitute, which opposes said first surface, is exposed to the tissue culture medium, but not to the gaseous environment.

2. The apparatus of claim 1, wherein:
(a) the first chamber comprises a gaseous environment having a relative humidity below 90% and comprising less than 5% $CO_2$, wherein optionally said gaseous environment is provided by an inflow of compressed air into the first chamber;
(b) the second chamber comprises tissue culture medium at a temperature of 33.0-37.5° C., optionally at 37° C., and a pH of 6.1-7.9; and/or
(c) the skin sample holder houses ex vivo mammalian skin and/or a mammalian skin substitute.

3. The apparatus of claim 1, wherein the epidermis of ex vivo mammalian skin or epidermis-equivalent of a mammalian skin substitute provides the first surface; and/or the dermis of ex vivo mammalian skin or dermis-equivalent of a mammalian skin substitute provides the second surface.

4. The apparatus of claim 1, wherein the ex vivo mammalian skin and/or skin substitute comprises stratum corneum, stratum granulosum, stratum spinosum, and/or stratum basale layers.

5. The apparatus of claim 4, wherein in use:
the stratum corneum layer is exposed to the gaseous environment, but not to the tissue culture medium; and/or
the stratum basale layer and/or the dermis or dermal equivalent is exposed to the tissue culture medium, but not to the gaseous environment.

6. The apparatus of claim 1, wherein the ex vivo mammalian skin and/or skin substitute is one of a plurality of ex vivo mammalian skin and/or skin substitute samples, wherein the plurality of samples are arranged in separate skin sample holders in an array format.

7. The apparatus of claim 1, wherein the apparatus comprises:
(a) one or more pumps, which pump tissue culture medium into and/or out of the second chamber, wherein optionally the flow rate is between 1 and 45 ml/min; and/or
(b) one or more pH probe(s), temperature probe(s), $CO_2$ sensor(s), and/or humidity sensor(s); and/or (c) a housing that encloses the first and second chambers, optionally wherein the housing additionally comprises a filter outlet, which is configured to enable the release of gases; and/or
(d) an inflow pipe which is configured to deliver gases into the first chamber, wherein optionally said gases comprise compressed air; and/or
(e) comprises a sample of ex vivo mammalian skin or a mammalian skin substitute, optionally wherein the skin substitute is recombinant human epidermis (RHE) or full thickness RHE (FT RHE).

8. The apparatus of claim 1, wherein the second chamber comprises tissue culture medium and said tissue culture medium is maintained at a temperature of 33.0-37.5° C. by the action of a heater.

9. The apparatus of claim 1, wherein said apparatus provides monitoring and feedback control of culture media pH, humidity and/or temperature.

10. The apparatus claim 1, wherein:
(a) immune cells are retained in the ex vivo mammalian skin and/or skin substitute following at least five days in culture; and/or
(b) epidermal cells of the ex vivo mammalian skin and/or skin substitute retain a normal lipid profile following at least three days in culture; and/or
(c) cells of the ex vivo mammalian skin and/or skin substitute express keratinocyte differentiation markers at normal detectable levels following at least five days in culture; and/or
(d) cells of the ex vivo mammalian skin and/or skin substitute do not have elevated K16 expression following at least five days in culture relative to baseline levels.

11. A method of culturing ex vivo mammalian skin and/or a mammalian skin substitute, the method comprising providing one or more samples of ex vivo mammalian skin and/or a mammalian skin substitute and culturing the one or more samples using the apparatus according to claim 1.

12. The method of claim 11, wherein said method comprises:
maintaining a first surface of the ex vivo mammalian skin or skin substitute in a gaseous environment comprising less than 5% $CO_2$, at a temperature below 37° C. and a relative humidity below 90%; and
maintaining a second surface of the ex vivo mammalian skin or skin substitute in a tissue culture medium at a temperature of 33.0-37.5° C. and pH of 6.1-7.9;
wherein the first surface is not exposed to the tissue culture medium; and the second surface is not exposed to the gaseous environment.

13. The method of claim 11, wherein the skin substitute is FT RHE or RHE.

14. The method of claim 11, wherein the gaseous environment:
(a) comprises 0.02-0.05% $CO_2$; and/or
(b) has a relative humidity of 40-50% RH; and/or
(c) is at a temperature of 18-25° C.; and/or
(d) is sterile.

15. The method of claim 11, wherein the tissue culture medium:
(a) flows under the dermis of the ex vivo skin or dermal equivalent of the FT-RHE at a flow rate ranging from 1 ml/min to 45 ml/min; and/or
(b) is at a temperature of 37° C.; and/or
(c) is maintained at pH 6.1-7.9.

16. The method of claim 11, wherein:
(a) immune cells are retained in the ex vivo mammalian skin and/or skin substitute following at least five days in culture;
(b) epidermal cells of the ex vivo mammalian skin and/or skin substitute retain a normal lipid profile following at least three days in culture;
(c) cells of the ex vivo mammalian skin and/or skin substitute express keratinocyte differentiation markers at normal detectable levels following at least five days in culture; and/or
(d) cells of the ex vivo mammalian skin and/or skin substitute do not have elevated K16 expression following at least five days in culture relative to baseline levels.

17. The method of claim 11, wherein said method comprises monitoring and feedback control of the pH, humidity, temperature, and/or flow rate of tissue culture medium.

18. The method according to claim 11, wherein:
(a) the barrier comprises a plastic and/or silicon gasket;
(b) the skin sample holder comprises a mesh and optionally the ex vivo skin or skin substitute is locatable on said mesh;
(c) the skin sample holder is a transwell insert;
(d) the skin sample or skin equivalent is: embedded in or surrounded by a gel; supported by a gel; or is inside a transwell;
(e) cells retain metabolic activity/viability for at least 5 days;
(f) epidermal skin surface properties of pH and moisture are maintained for 7 days;
(g) the tissue culture medium flows through the second chamber at a flow rate ranging from 0.01 ml/min to 45 ml/min;
(h) the tissue culture medium is at a temperature of 33-37° C.;
(i) the tissue culture medium is maintained at pH 6.1-7.9; and/or
(j) the tissue culture medium is maintained at an oxygen saturation level of 0.2-15% O2;
(k) said method comprises monitoring and/or feedback control of $CO_2$, humidity, temperature and/or flow rate within the gaseous environment;
(l) the first surface is an epidermal cornified layer and/or the second surface is the dermis and/or hypodermis;
(m) the epidermal cornified layer thickness of said ex vivo mammalian skin and/or skin substitute remains constant or substantially constant, relative to said thickness at day 0, during at least 1, 2, 3, 4, 5, 6, or 7 days of culture in said apparatus; and/or
(n) the epidermal cornified layer thickness of said ex vivo mammalian skin and/or skin substitute remains constant, relative to said thickness at day 0, during at least 7 days of culture in said apparatus.

* * * * *